(12) United States Patent
Yu

(10) Patent No.: US 8,349,866 B2
(45) Date of Patent: Jan. 8, 2013

(54) HIGH PENETRATION PRODRUG COMPOSITIONS OF 1H-IMIDAZO[4,5-C]QUINOLIN-4-AMINES AND 1H-IMIDAZO[4,5-C]QUINOLIN-4-AMINE-RELATED COMPOUNDS

(76) Inventor: Chongxi Yu, Plainfield, IL (US)

( * ) Notice: Subject to any disclaimer, the term of this patent is extended or adjusted under 35 U.S.C. 154(b) by 364 days.

(21) Appl. No.: 12/534,096

(22) Filed: Jul. 31, 2009

(65) Prior Publication Data

US 2010/0021394 A1  Jan. 28, 2010

Related U.S. Application Data

(63) Continuation-in-part of application No. PCT/IB2007/050322, filed on Jan. 31, 2007.

(51) Int. Cl.
*A61K 31/44* (2006.01)
*C07D 471/00* (2006.01)
*C07D 215/38* (2006.01)

(52) U.S. Cl. ............................. 514/293; 546/82; 546/159

(58) Field of Classification Search .................. 514/293; 546/82, 159
See application file for complete search history.

(56) References Cited

U.S. PATENT DOCUMENTS

| 4,411,893 A | 10/1983 | Johnson et al. |
| 4,689,338 A | 8/1987 | Gerster |
| 4,698,348 A | 10/1987 | Gerster |
| 4,722,941 A | 2/1988 | Eckert et al. |
| 4,746,515 A | 5/1988 | Cheng et al. |
| 4,751,087 A | 6/1988 | Wick |
| 5,736,553 A | 4/1998 | Wick et al. |

FOREIGN PATENT DOCUMENTS

| WO | WO 93/25197 | 12/1993 |
| WO | WO 2005/025583 A2 | 3/2005 |
| WO | WO 2005/110013 A2 | 11/2005 |
| WO | WO 2007/149802 A2 | 12/2007 |

OTHER PUBLICATIONS

The Merriam-Webster Online Dictionary, obtained online at : http://www.merriam-webster.com/dictionary/related, obtained online on: Jan. 13, 2012.*
Wermuth, Drug Discovery Today, 2006, 11(7/8), 348-354.*
The Merriam-Webster Online Dictionary, obtained online at : http://www.merriam-webster.com/dictionary/derivative, obtained online on: Jan. 13, 2012.*
Quality Biological Inc., Material Safety Data Sheet, obtained online at: www.qualitybiological.com/ptistore/resource/msda/112-024.pdt, downloaded on: Jan. 13, 2012.*
Bamford, M.J., et al., "(1H-Imidazo[4,5-c]Pyridin-2-yl)-1,2,5-Oxadiazol-3-Ylamine Derivatives: Further Optimisation as Highly Potent and Selective MSK-1-Inhibitors," Bioorganic & Medicinal Chemistry Letters 15:3407-3411 (2005).
Berge, S.M., et al., "Pharmaceutical Salts," J. Pharm. Sci. 66(1):1-19 (1977).
Gerster, J.F., et al., "Synthesis and Structure-Activity Relationships of 1H-Imidazo[4,5-c]Quinolines That Induce Interferon Production," J. Med. Chem. 48(10):3481-3491 (2005).
Goblyos, A., et al., "Structure-Activity Relationships of New 1H-Imidazo[4,5 c]Quinolin-4-Amine Derivatives as Allosteric Enhancers of the A3 Adenosine Receptor," J. Med. Chem. 49(11):3354-3361 (2006).
Kern, E.R., et al., "Treatment of Experimental Herpesvirus Infections with Phosphonoformate and Some Comparisons with Phosphonoacetate," Antimicrob. Agents Chemother. 14(6);817-823 (1978).
Korean Intellectual Property Office, International Preliminary Report on Patentability for PCT/IB2007/050322, dated Aug. 4, 2009.
Milosovich, S., et al., "Testosteronyl-4-Dimethylaminobutyrate-HCl: A Prodrug with Improved Skin Penetration Rate," J. Pharm. Sci. 82(2):227-228 (1993).
Silverman, R.B., "The Organic Chemistry of Drug Design and Drug Action," Academic Press Inc. 1992, pp. 355-361.

* cited by examiner

Primary Examiner — Abigail Fisher
(74) Attorney, Agent, or Firm — Perkins Coie LLP; Yingli Wang

(57) ABSTRACT

The invention provides compositions of novel high penetration compositions (HPC) or high penetration prodrugs (HPP) of 1H-imidazo[4,5-c]quinolin-4-amines and 1H-imidazo[4,5-c]quinolin-4-amine-related compounds, which are capable of crossing biological barriers with high penetration efficiency. The HPPs are capable of being converted to parent active drugs or drug metabolites after crossing the biological barrier and thus can render treatments for the conditions that the parent drugs or metabolites can. Additionally, the HPPs are capable of reaching areas that parent drugs may not be able to access or to render a sufficient concentration at the target areas and therefore render novel treatments. The HPPs can be administered to a subject through various administration routes, e.g., locally delivered to an action site of a condition with a high concentration or systematically administered to a biological subject and enter the general circulation with a faster rate.

4 Claims, 1 Drawing Sheet

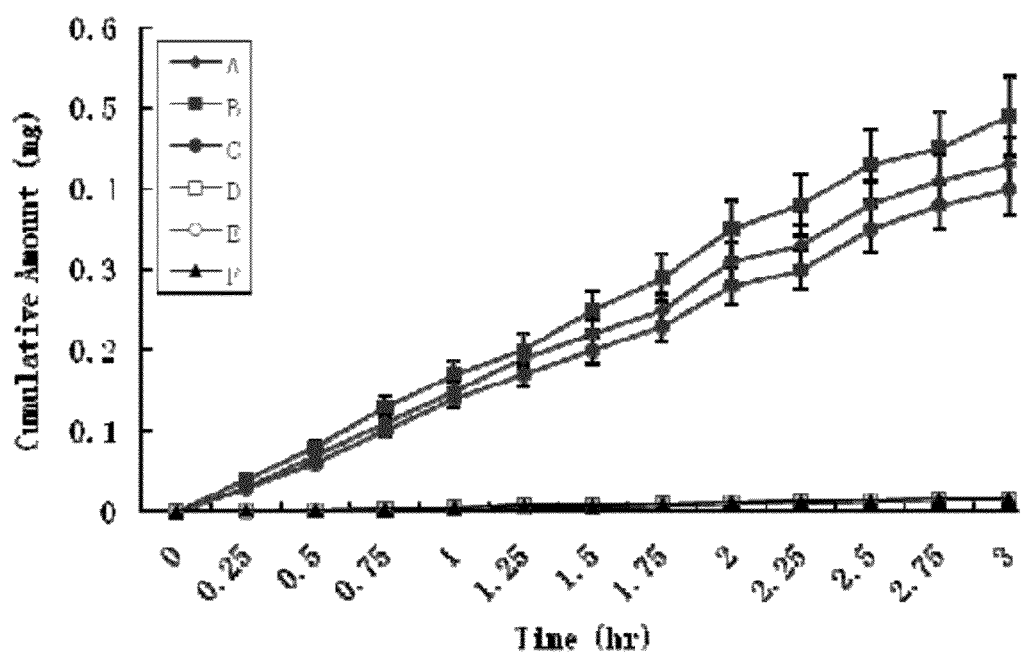

HIGH PENETRATION PRODRUG COMPOSITIONS OF 1H-IMIDAZO[4,5-C] QUINOLIN-4-AMINES AND 1H-IMIDAZO[4,5-C]QUINOLIN-4-AMINE-RELATED COMPOUNDS

CROSS-REFERENCE TO RELATED APPLICATIONS

The present application is a continuation-in-part application of International Application PCT/IB2007/050322, filed Jan. 31, 2007 and published Aug. 7, 2008 with International Publication Number WO/2008/093173, which is incorporated herein by reference in its entirety.

FIELD OF THE INVENTION

This invention relates to the field of pharmaceutical compositions capable of penetrating one or more biological barriers and methods of using the pharmaceutical compositions for preventing, diagnosing and/or treating conditions or diseases in humans and animals that are treatable by 1H-imidazo[4,5-c]quinolin-4-amines or 1H-imidazo[4,5-c]quinolin-4-amine-related compounds. The invention also relates to methods of using the pharmaceutical compositions for screening new drug candidates and methods of using the pharmaceutical compositions for diagnosing a condition in a biological subject.

BACKGROUND OF THE INVENTION

1H-Imidazo[4,5-c]quinolin-4-amines and 1H-Imidazo[4,5-c]quinolin-4-amine-related compounds have been used as antiviral agents to treat lesions caused by herpes simplex virus.

A variety of formulations for topical administration of 1H-Imidazo[4,5-c]quinolin-4-amines and 1H-Imidazo[4,5-c]quinolin-4-amine-related compounds have been developed, such as Aldara (1-Isobutyl-1H-imidazo[4,5-c]quinolin-4-amine) cream developed by 3M for the treatment of actinic keratosis, superficial basal cell carcinoma, and external genital and perianal warts.

However, 1H-imidazo[4,5-c]quinolin-4-amines and 1H-Imidazo[4,5-c]quinolin-4-amine-related compounds have low solubility in water and organic solvents and their skin penetration rates are low. The cream compositions may keep the drug on the skin for prolonged period of time in high concentration and cause side effects such as redness, swelling, sores, blisters, or ulcers, skin that becomes hard or thickened, skin peeling, scabbing and crusting, itching, burning and changes in skin color that may become permanent. Moreover, due to the poor penetration ability, these compounds are not very effective to treat many cancers, except superficial basal cell carcinoma.

Therefore, a need exists in the art for novel compositions that are capable of being delivered efficiently and effectively to the action site of a condition (e.g., a disease) to prevent, reduce or treat conditions as well as minimize adverse side effects.

SUMMARY OF THE INVENTION

One aspect of the invention is directed to a high penetration prodrug (HPP) or high penetration composition (HPC) comprising a functional unit covalently linked to a transportational unit through a linker. The terms "HPP" and "HPC" are used alone or together herein and are interchangeable unless specifically noted.

In certain embodiments, a functional unit of a HPP or HPC comprises a moiety of an agent, wherein the efficient and effective delivery of the agent to a biological subject and/or transportation of the agent across one or more biological barriers are/is desired.

In certain embodiments, a functional unit may be hydrophilic, lipophilic, or amphiphilic (i.e., both hydrophilic and lipophilic). For example, the lipophilic nature of a function unit may be inherent or achieved by converting the hydrophilic moieties of a functional unit to lipophilic moieties. In certain embodiments, a carboxyl group, amino group, guanidine group or other hydrophilic group of a functional unit is protected with an alkyl, aryl, or heteroaryl ester or amide group to make the HPP or HPC more lipophilic.

In certain embodiments, a functional unit of a HPP or HPC comprises a moiety of a 1H-imidazo[4,5-c]quinolin-4-amines or 1H-imidazo[4,5-c]quinolin-4-amine-related compound. A 1H-imidazo[4,5-c]quinolin-4-amine-related compound is a compound comprising a 1H-imidazo[4,5-c]quinolin-4-amine structure, a 1H-imidazo[4,5-c]quinolin-4-amine metabolite, or an agent that can be metabolized into a 1H-imidazo[4,5-c]quinolin-4-amine or 1H-imidazo[4,5-c]quinolin-4-amines metabolite after a HPP or HPC penetrates one or more biological barriers. A 1H-imidazo[4,5-c]quinolin-4-amine-related compound further includes a compound that is an analog or mimic of a 1H-imidazo[4,5-c]quinolin-4-amine or a 1H-imidazo[4,5-c]quinolin-4-amine metabolite, or an agent that can be metabolized into an analogue or mimic of a 1H-imidazo[4,5-c]quinolin-4-amine or a 1H-imidazo[4,5-c]quinolin-4-amine metabolite, after a HPP or HPC penetrates one or more biological barriers. Examples of 1H-imidazo[4,5-c]quinolin-4-amines include, without limitation, 1-isobutyl-1H-imidazo[4,5-c]quinolin-4-amine, 1-benzyl-1H-imidazo[4,5-c]quinolin-4-amine, 1,8-dimethyl-1H-imidazo[4,5-c]quinolin-4-amine, 1,2-dimethyl-1H-imidazo[4,5-c]quinolin-4-amine, 1-(2,3-dihydroxypropyl)-1H-imidazo[4,5-c]quinolin-4-amine, 1-cyclohexylmethyl-1H-imidazo[4, 5-c]quinolin-4-amine, 1-benzyl-2-methyl-1H-imidazo[4,5-c]quinolin-4-amine, 1-n-hexyl-2-methyl-1H-imidazo[4,5-c]quinolin-4-amine, 1-methyl-1H-imidazo[4,5-c]quinolin-4-amine, 1-(2-hydroxyethyl)-1H-imidazo[4,5-c]quinolin-4-amine, 1,2,8-trimethyl-1H-imidazo[4,5-c]quinolin-4-amine, 1-n-hexyl-1H-imidazo[4,5-c]quinolin-4-amine, and 1-butyl-1H-imidazo[4,5-c]quinolin-4-amine.

In certain embodiments, a transportational unit of a HPP or HPC comprises a protonatable amine group that is capable of facilitating or enhancing the transportation or crossing of the HPP or HPC through one or more biological barriers. In certain embodiments, the protonatable amine group is substantially protonated at the pH of the biological barriers through which a HPP or HPC penetrates. In certain embodiments, the amine group can be reversibly protonated or deprotonated.

In certain embodiments, a linker covalently links the functional unit to the transportational unit of a HPP and comprises a bond that is capable of being cleaved after the HPP penetrates across one or more biological barriers. The cleavable bond comprises, for example, a covalent bond, an ether, a thioether, an amide, an ester, a thioester, a carbonate, a carbamate, a phosphate or an oxime bond.

In certain embodiments, a HPP or HPC of a 1H-imidazo[4,5-c]quinolin-4-amine or 1H-imidazo[4,5-c]quinolin-4-amine-related compound comprises one or two primary, secondary or tertiary amine groups that exist in the protonated form at physiological pH. In certain embodiments, the HPP or HPC comprises one primary, secondary or tertiary amine group that exists in the protonated form at physiological pH.

Another aspect of the invention relates to a pharmaceutical composition comprising at least one HPP or HPC of a 1H-imidazo[4,5-c]quinolin-4-amine or 1H-imidazo[4,5-c] quinolin-4-amine-related compound and a pharmaceutically acceptable carrier.

Another aspect of the invention relates to a method for penetrating a biological barrier using a HPP or HPC of a 1H-imidazo[4,5-c]quinolin-4-amine or 1H-imidazo[4,5-c] quinolin-4-amine-related compound.

Another aspect of the invention relates to a method for diagnosing the onset, development, or remission of a condition in a biological subject by using a HPP or HPC of a 1H-imidazo[4,5-c]quinolin-4-amine or 1H-imidazo[4,5-c] quinolin-4-amine-related compound. In certain embodiments, the HPP (or HPC) or the functional unit thereof is detectable. In certain embodiments, the HPP or the functional unit of the HPP is inherently detectable, labeled with, or conjugated to, a detectable marker.

Another aspect of the invention relates to a method for screening functional units, linkers, or transportational units for desired characteristics.

Another aspect of the invention relates to a method for preventing, ameliorating, or treating a condition in a biological subject by administering to the subject a composition in accordance with the invention. In certain embodiments, the method relates to treating a condition in a subject treatable by 1H-imidazo[4,5-c]quinolin-4-amines or 1H-imidazo[4,5-c] quinolin-4-amine-related compounds and their HPP or HPC by administering to the subject a therapeutically effective amount of a HPP of a 1H-imidazo[4,5-c]quinolin-4-amine or 1H-imidazo[4,5-c]quinolin-4-amine-related compound, or a pharmaceutical composition thereof. In certain embodiments, the conditions treatable by the method include, without limitation, rheumatoid arthritis, eczema, psoriasis, multiple sclerosis, essential thrombocythaemia, viral diseases and related conditions such as warts (such as genital and perianal warts, common wart, flat wart, filiform wart, mosaic wart, and any other warts), Actinic Keratosis, flu (such as bird flu(Influenza), swine flu, and any other flu which is caused by influenzavirus A (which includes, but are not limited to H1N1, H2N2, H3N2, H5N1, H7N7, H1N2, H9N2, H7N2, H7N3, H10N7), Influenzavirus B, and/or Influenzavirus C), hepatitis, Severe Acute Respiratory Syndrome (SARS), pneumonia, and acquired immunodeficiency syndrome (AIDS), and tumor and related conditions such as benign tumor, breast cancer, oral cancer, colon-rectum cancer, lung or other respiratory system cancers, skin cancer, superfacial basal cell carcinoma, basal cell carcinoma, cervical cancer, mycosis fungoides, Kaposi's sarcoma, AIDS-related Kaposi's sarcoma, systemic Kaposi's sarcoma, cutaneous T-cell lymphoma (CTCL), squamous cell skin cancer, second primary tumors, head and neck carcinoma, ovarian cancer, prostate cancer, and renal cell cancer.

In certain embodiments, a pharmaceutical composition of a HPP or HPC is administrated to a biological subject via various routes including, but not limited to, oral, enteral, buccal, nasal, topical, rectal, vaginal, aerosol, transmucosal, epidermal, transdermal, dermal, ophthalmic, pulmonary, subcutaneous, and/or parenteral routes. In certain preferred embodiments, a pharmaceutical composition of a HPP or HPC is administered orally, transdermally, topically, subcutaneously and/or parenterally.

In accordance with the advantages of the invention, without intending to be limited by any particular mechanism, a therapeutically effective amount of a HPP or HPC can be administered locally to a site of condition with a less dosage at a higher concentration. The advantages of the invention also include, for example, avoidance of systematic administration, reduction of adverse effects (e.g., pain of injection, gastrointestinal/renal effects, and other side effect), and possible novel treatments due to high local concentration of a HPP, HPC or active agent. The advantages further include, for example, systematic administration of a HPP or HPC to a biological subject to achieve faster and more efficient bioavailability, penetration of biological barriers (e.g., the blood brain barrier) which have been difficult to cross, and new indications as a result of passing through biological barriers.

BRIEF DESCRIPTION OF THE FIGURES

FIG. 1: Cumulative amounts of sarcosine 1-isobutyl-1H-imidazo[4,5-c]quinolin-4-amide hydrochloride (3% solution, A), sarcosine 1-butyl-1H-imidazo[4,5-c]quinolin-4-amide hydrochloride (3% solution, B), sarcosine 1-benzyl-1H-imidazo[4,5-c]quinolin-4-amide hydrochloride (3% solution, C), 1-isobutyl-1H-imidazo[4,5-c]quinolin-4-amine hydrochloride (3% suspension, D), 1-butyl-1H-imidazo[4,5-c]quinolin-4-amine hydrochloride (3% suspension, E), and 1-benzyl-1H-imidazo[4,5-c]quinolin-4-amine hydrochloride (3% suspension, F), crossing isolated human skin tissue in Franz cells (n=5). In each case, the vehicle was a mixture of ethanol/pH 7.4 phosphate buffer (0.2 M) (v/v, 70/30).

DETAILED DESCRIPTION OF THE INVENTION

I. Structures of High Penetration Prodrug (HPP) or High Penetration Composition (HPC)

One aspect of the invention is directed to a high penetration prodrug (HPP) or a high penetration composition (HPC). The term "high penetration prodrug" or "HPP" or "high penetration composition" or "HPC" as used herein refers to a composition comprising a functional unit covalently linked to a transportational unit through a linker.

A functional unit of a HPP or HPC which comprises a moiety of a parent drug has the properties of: 1) the delivery of the parent drug or the HPP/HPC into a biological subject and/or the transportation of the parent drug across a biological barrier are/is desired, 2) the HPP/HPC is capable of penetrating or crossing a biological barrier, and 3) the HPP/HPC is capable of being cleaved so as to turn the moiety of a parent drug into the parent drug or a metabolite of the parent drug.

In certain embodiments, a functional unit may be hydrophilic, lipophilic, or amphiphilic (hydrophilic and lipophilic). The lipophilic moiety of the functional unit may be inherent or achieved by converting one or more hydrophilic moieties of the functional unit to lipophilic moieties. For example, a lipophilic moiety of a functional unit is produced by converting one or more hydrophilic groups of the functional unit to lipophilic groups via organic synthesis. Examples of hydrophilic groups include, without limitation, carboxylic, hydroxyl, thiol, amine, phosphate/phosphonate, guanidine and carbonyl groups. Lipophilic moieties produced via the modification of these hydrophilic groups include, without limitation, ethers, thioethers, esters, thioesters, carbonates, carbamates, amides, phosphates and oximes. In certain embodiments, a functional unit is lipophilicized by acetylation. In certain embodiments, a functional unit is lipophilicized by esterification.

In certain embodiments, a parent drug of a HPP or HPC is selected from the group consisting of a 1H-imidazo[4,5-c]quinolin-4-amine and 1H-imidazo[4,5-c]quinolin-4-amine-related compound. The moiety of a 1H-imidazo[4,5-c]quinolin-4-amine or 1H-imidazo[4,5-c]quinolin-4-amine-related compound can be further converted to a lipophilic moiety as described supra.

1H-imidazo[4,5-c]quinolin-4-amines are well known in the art and are used in connection with various conditions. As used herein, a 1H-imidazo[4,5-c]quinolin-4-amine refers to a compound that comprises the following structure A:

Structure A

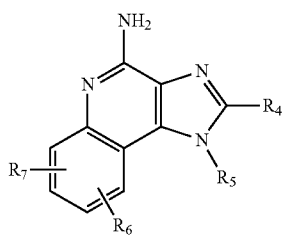

including stereoisomers and pharmaceutically acceptable salts thereof, wherein:
- $R_4$ is selected from the group consisting of hydrogen, $R_b$, —$R_b$OH, —$R_aOR_b$, —$R_aOC(=O)R_b$, and —$R_aC(=O)OR_b$;
- $R_5$ is selected from the group consisting of hydrogen, $R_b$, —$R_b$OH, —$R_aOR_b$, —$R_aOC(=O)R_b$, —$R_aC(=O)R_b$, and —$R_aC(=O)OR_b$;
- $R_6$ is selected from the group consisting of hydrogen, substituted and unsubstituted alkyl, substituted and unsubstituted alkoxyl, and halogen;
- $R_7$ is selected from the group consisting of hydrogen, substituted and unsubstituted alkyl, substituted and unsubstituted alkoxy, and halogen;
- $R_a$ is selected from the group consisting of nothing, substituted and unsubstituted alkyl, and substituted and unsubstituted aryl group;
- $R_b$ is selected from the group consisting of substituted and unsubstituted alkyl, and substituted and unsubstituted aryl group; and
- any $CH_2$ groups of all $R_4$, $R_5$, $R_6$, $R_7$, $R_a$ and $R_b$ may be replaced with O, S, or NH.

Examples of 1H-imidazo[4,5-c]quinolin-4-amines include without limitation, chemicals comprising a structure selected from the group consisting of Structure R1, Structure R2, Structure R3, Structure R4, Structure R5, Structure R6, Structure R7, Structure R8, Structure R9, Structure R10, Structure R11, Structure R12, Structure R13, Structure R14, Structure R15, Structure R16, Structure R17, and Structure R18:

Structure R1

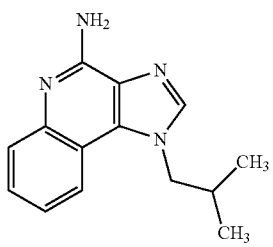

Structure R2

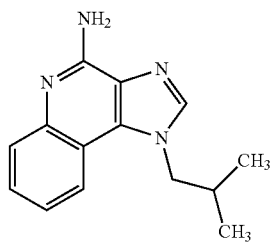

Structure R3

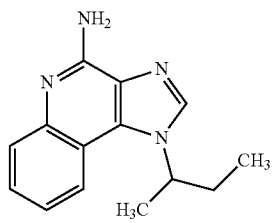

Structure R4

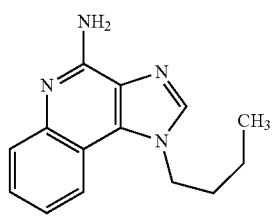

Structure R5

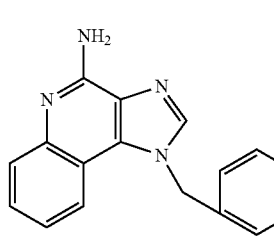

Structure R6

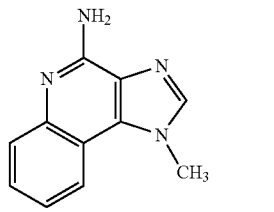

Structure R7

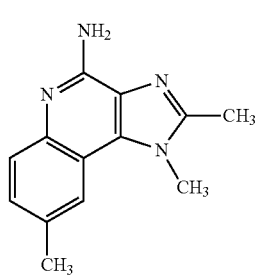

Structure R8

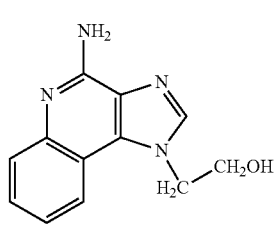

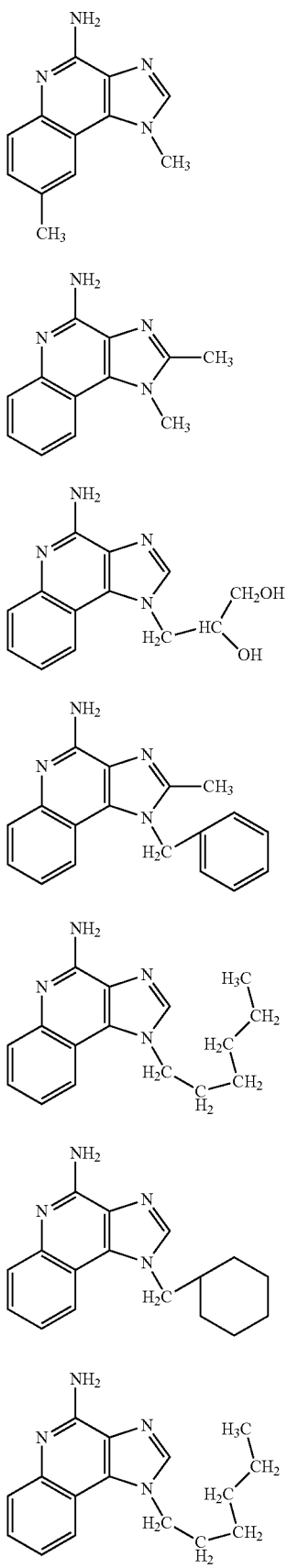
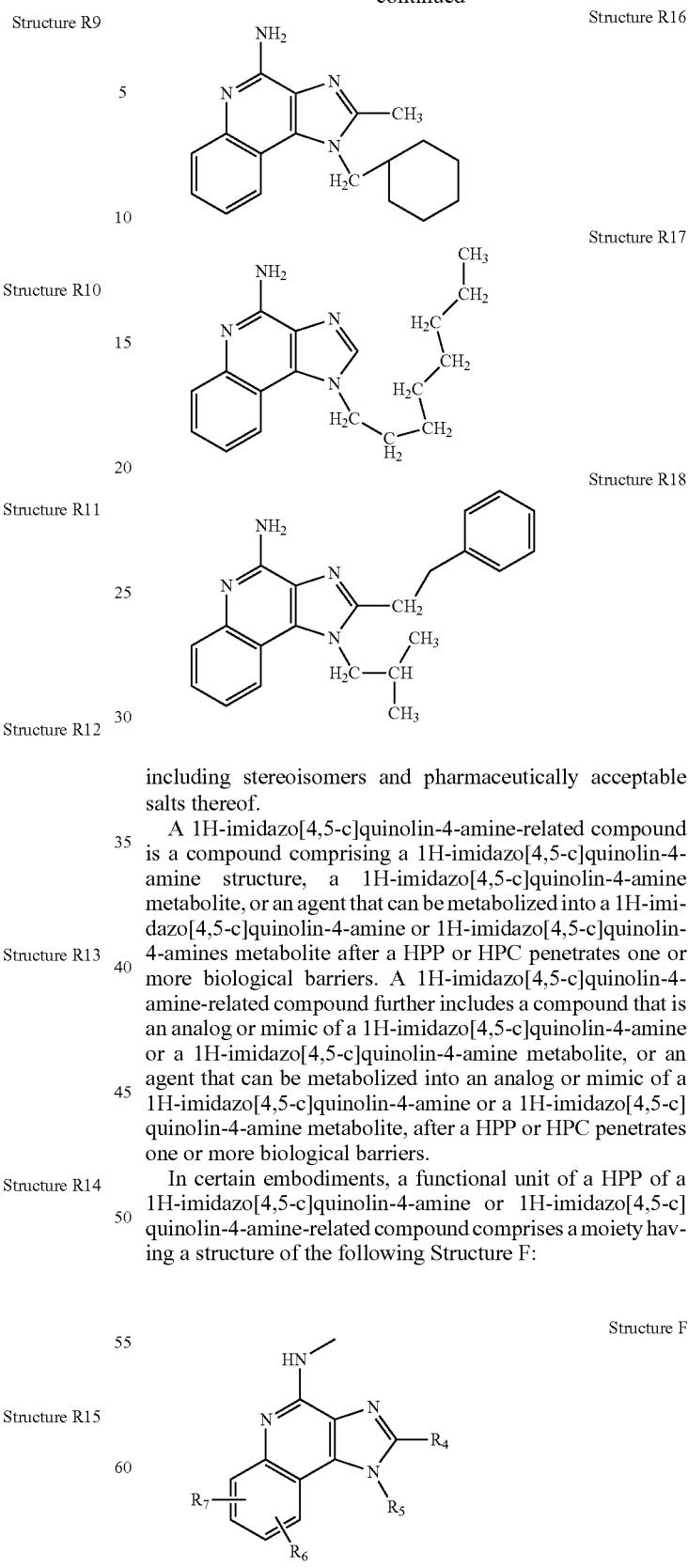

including stereoisomers and pharmaceutically acceptable salts thereof.

A 1H-imidazo[4,5-c]quinolin-4-amine-related compound is a compound comprising a 1H-imidazo[4,5-c]quinolin-4-amine structure, a 1H-imidazo[4,5-c]quinolin-4-amine metabolite, or an agent that can be metabolized into a 1H-imidazo[4,5-c]quinolin-4-amine or 1H-imidazo[4,5-c]quinolin-4-amines metabolite after a HPP or HPC penetrates one or more biological barriers. A 1H-imidazo[4,5-c]quinolin-4-amine-related compound further includes a compound that is an analog or mimic of a 1H-imidazo[4,5-c]quinolin-4-amine or a 1H-imidazo[4,5-c]quinolin-4-amine metabolite, or an agent that can be metabolized into an analog or mimic of a 1H-imidazo[4,5-c]quinolin-4-amine or a 1H-imidazo[4,5-c]quinolin-4-amine metabolite, after a HPP or HPC penetrates one or more biological barriers.

In certain embodiments, a functional unit of a HPP of a 1H-imidazo[4,5-c]quinolin-4-amine or 1H-imidazo[4,5-c]quinolin-4-amine-related compound comprises a moiety having a structure of the following Structure F:

including stereoisomers and pharmaceutically acceptable salts thereof, wherein:

$R_4$ is selected from the group consisting of hydrogen, $R_b$, —$R_bOH$, —$R_aOR_b$, $R_aOC(=O)R_b$, and —$R_bC(=O)OR_b$;

$R_5$ is selected from the group consisting of hydrogen, $R_b$, —$R_bOH$, —$R_aOR_b$, —$R_aOC(=O)R_b$, —$R_aC(=O)R_b$, and —$R_aC(=O)OR_b$;

$R_6$ is selected from the group consisting of hydrogen, substituted and unsubstituted alkyl, substituted and unsubstituted alkoxyl, and halogen, $R_7$ is selected from the group consisting of hydrogen, substituted and unsubstituted alkyl, substituted and unsubstituted alkoxy and halogen;

$R_a$ is selected from the group consisting of nothing, substituted and unsubstituted alkyl, and substituted and unsubstituted aryl group;

$R_b$ is selected from the group consisting of substituted and unsubstituted alkyl, and substituted and unsubstituted aryl group; and any $CH_2$ groups of all $R_4$, $R_5$, $R_6$, $R_7$, $R_a$ and $R_b$ may be replaced with O, S, or NH.

In certain embodiments, a functional unit of a HPP of a 1H-imidazo[4,5-c]quinolin-4-amine or 1H-imidazo[4,5-c]quinolin-4-amine-related compound comprises a moiety having a structure of Structure F as defined supra, wherein:

$R_4$ is selected from the group consisting of alkyl of 1 to about 10 carbon atoms, hydroxylalkyl of 1 to about 10 carbon atoms, acyloxyalkyl wherein the acyloxy moiety is alkanoyloxy of 2 to about 5 carbon atoms or benzoyloxy, and the alkyl moiety contains 1 to about 8 carbon atoms, benzyl, (phenyl)ethyl and phenyl, said benzyl, (phenyl)ethyl or phenyl substituent being optionally substituted on the benzene ring by 1 or 2 moieties independently selected from the group consisting of alkyl of 1 to about 5 carbon atoms, alkoxy of 1 to about 5 carbon atoms and halogen, with the proviso that if said benzene ring is substituted by 2 of said moieties, then said moieties together contain no more than 8 carbon atoms;

$R_5$ is selected from the group consisting of hydrogen, alkyl of 1 to about 10 carbon atoms, benzyl, (phenyl)ethyl and phenyl, said benzyl, (phenyl)ethyl or phenyl substituent being optionally substituted on the benzene ring by 1 or 2 moieties independently selected from the group consisting of alkyl of 1 to about 5 carbon atoms, alkoxy of 1 to about 5 carbon atoms and halogen, with the proviso that if said benzene ring is substituted by 2 of said moieties, then said moieties together contain no more than 8 carbon atoms;

$R_6$ is selected from the group consisting of alkyl of 1 to about 5 carbon atoms, and alkoxy of 1 to about 5 carbon atoms and halogen; and $R_7$ is selected from the group consisting of alkyl of 1 to about 5 carbon atoms, and alkoxy of 1 to about 5 carbon atoms and halogen.

In certain embodiments, a functional unit of a HPP of a 1H-imidazo[4,5-c]quinolin-4-amine or 1H-imidazo[4,5-c]quinolin-4-amine-related compound comprises a moiety having a structure selected from the group consisting of Structure F-1, Structure F-2, Structure F-3, Structure F-4, Structure F-5, Structure F-6, Structure F-7, Structure F-8, Structure F-9, Structure F-10, Structure F-11, Structure F-12, Structure F-13, Structure F-14, Structure F-15, Structure F-16, Structure F-17, and Structure F-18:

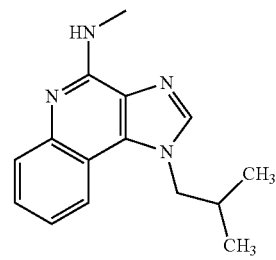

Structure F-1

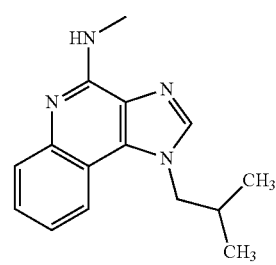

Structure F-2

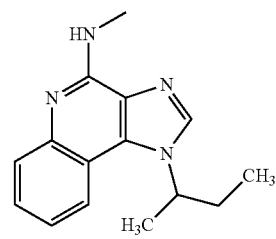

Structure F-3

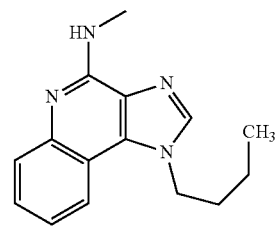

Structure F-4

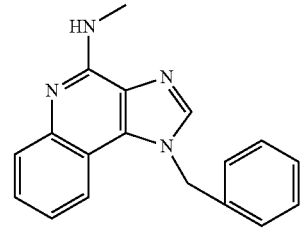

Structure F-5

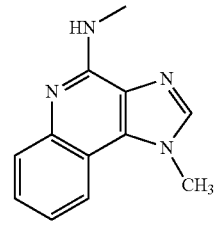

Structure F-6

Structure F-7
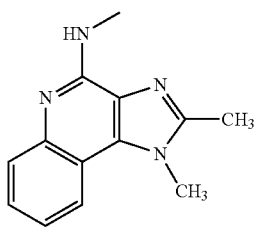

Structure F-8
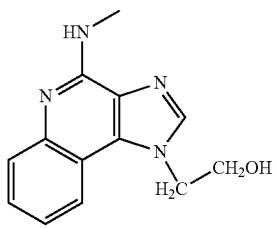

Structure F-9
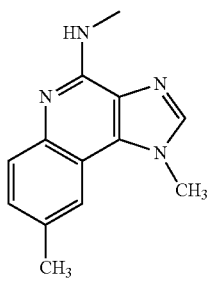

Structure F-10
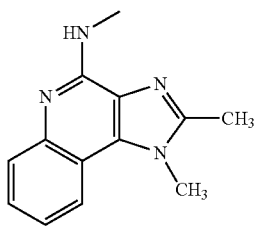

Structure F-11
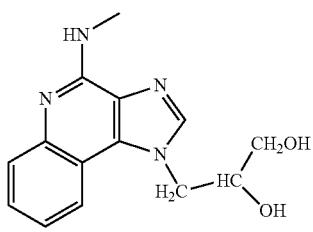

Structure F-12
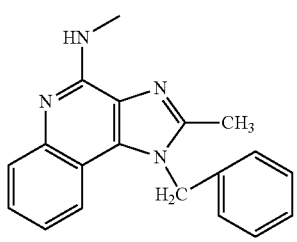

Structure F-13
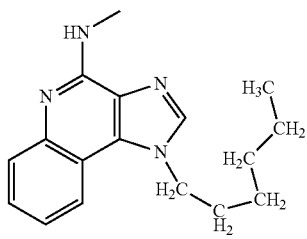

Structure F-14
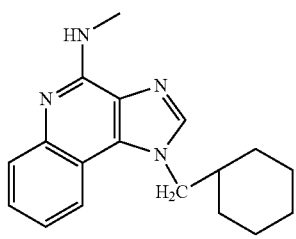

Structure F-15
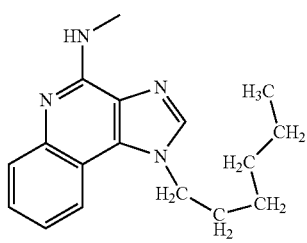

Structure F-16
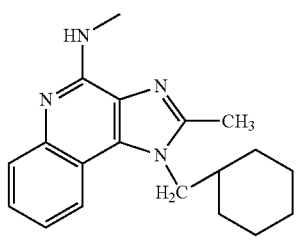

Structure F-17
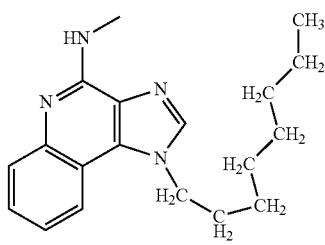

Structure F-18
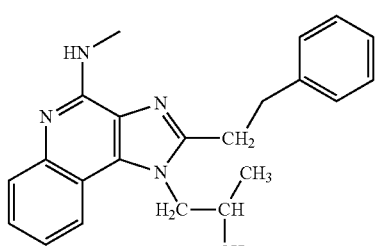

including stereoisomers and pharmaceutically acceptable salts thereof.

As used herein, the term "pharmaceutically acceptable salt" means those salts of compounds of the invention that are safe for application in a subject. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, the term "pharmaceutically acceptable acid" means acids that can form salts with compounds of the invention that are safe for application in a subject. Examples of pharmaceutically acceptable acid include, but are not limited to, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 30 carbons. In certain embodiments, the hydrocarbon group contains 1 to 20 carbons. In certain embodiments, the hydrocarbon group contains 1 to 12 carbons. In certain embodiments, the hydrocarbon group contains 1 to 6 carbons.

As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons. In certain embodiments, the hydrocarbon group contains 1 to 10 carbons. In certain embodiments, the hydrocarbon group contains 1 to 6 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —$CH_2$—OH, —$OCH_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, -alkyl-F, -alkyl-Cl, -alkyl-Br, -alkyl-I, -alkyl(F)—, -alkyl(Cl)—, -alkyl(Br)- and -alkyl(I)-.

As used herein, unless specified otherwise, the term "alkylthio" means an alkyl, cycloalkyl or heterocycloalkyl, which contains one or more sulfur atoms. Examples of alkylthio include, but are not limited to, —$CH_2$—SH, —$SCH_3$, —S-alkyl, -alkyl-SH, -alkyl-5-alkyl-, wherein the two alkyls can be the same or different.

As used herein, unless specified otherwise, the term "alkylamino" means an alkyl, cycloalkyl or heterocycloalkyl, which contains one or more nitrogen atoms. Examples of alkylamino include, but are not limited to, —$CH_2$—NH, —$NCH_3$, —N(alkyl)-alkyl, —N-alkyl, -alkyl-$NH_2$, -alkyl-N-alkyl and -alkyl-N(alkyl)-alkyl wherein the alkyls can be the same or different.

As used herein, unless specified otherwise, the term "alkylcarbonyl" means an alkyl, cycloalkyl or heterocycloalkyl, which contains one or more carbonyl groups. Examples of alkylcarbonyl group include, but are not limited to, aldehyde group (—$R_a$—C(=O)—H), ketone group (—R—C(=O)—R'), carboxylic acid group (R—C(=O)OH), ester group (—R—C(=O)O—R'), carboxamide, (—R—C(=O)O—N(R')R''), enone group (—R—C(=O)—C(R')=C(R'')R'''), acyl halide group (—R—C(=O)—X) and acid anhydride group (—R—C(=O)—O—C(=O)—R'), wherein R, R', R'' and R''' are the same or different alkyl, cycloalkyl, or heterocycloalkyl.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino and benzothiazolyl.

In certain embodiments, a transportational unit of a HPP comprises a protonatable amine group that is capable of facilitating the transportation or crossing of the HPP through one or more biological barriers (e.g., >about 5 times, >about 25 times, >about 50 times, >about 100 times, >about 300 times, >about 500 times faster than the parent drug). In certain embodiments, the protonatable amine group is substantially protonated at a physiological pH. In certain embodiments, the amine group can be reversibly protonated. In certain embodiments, the transportational unit may or may not be cleaved from the functional unit after the penetration of HPP through one or more biological barriers.

In certain embodiments, the protonatable amine group is selected from the group consisting of pharmaceutically acceptable substituted and unsubstituted primary amine groups, pharmaceutically acceptable substituted and unsubstituted secondary amine groups, and pharmaceutically acceptable substituted and unsubstituted tertiary amine groups.

In certain embodiments, the protonatable amine group is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr:

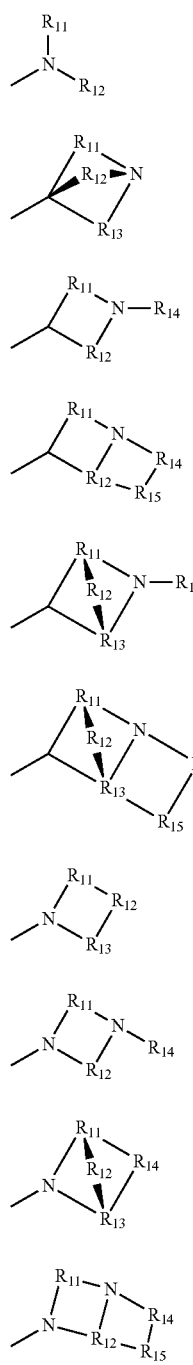
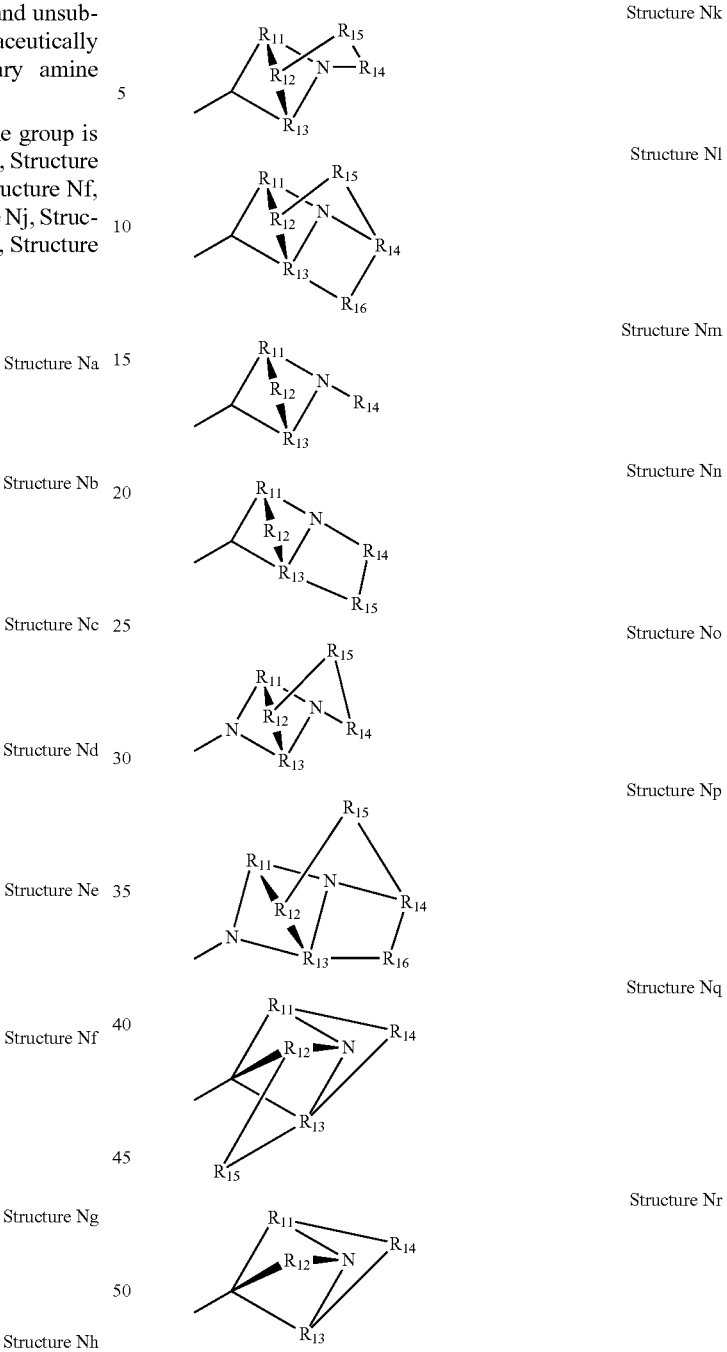

including stereoisomers and pharmaceutically acceptable salts thereof.

As used herein, unless specified otherwise, each $R_{11}$-$R_{16}$ is independently selected from the group consisting of nothing, H, $CH_2C(=O)OR_{11}$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_{11}$, or any other pharmaceutically acceptable groups.

In certain embodiments, a linker covalently linking a functional unit and a transportational unit of a HPP comprises a bond that is capable of being cleaved after the HPP penetrates across one or more BBs. The cleavable bond comprises, for example, a covalent bond, an ether, thioether, amide, ester, thioester, carbonate, carbamate, phosphate or oxime bond.

In certain embodiments, a HPP of a 1H-imidazo[4,5-c]quinolin-4-amine and 1H-imidazo[4,5-c]quinolin-4-amine-related compound has the following Structure L-1:

F-L$_4$-L$_2$-T            Structure L-1 including stereoisomers and pharmaceutically acceptable salts thereof, wherein:

F is a functional unit of a HPP of a 1H-imidazo[4,5-c]quinolin-4-amine or 1H-imidazo[4,5-c]quinolin-4-amine-related compound. Examples of F include Structure F, Structure F-1 to Structure F-18 as defined supra;

T is a transportational unit of a HPP of a 1H-imidazo[4,5-c]quinolin-4-amine or 1H-imidazo[4,5-c]quinolin-4-amine-related compound. For example, T is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra;

L$_2$ is selected from the group consisting of nothing, O, S, —N(L$_3$)-, —N(L$_3$)-CH$_2$—O, —N(L$_3$)-CH$_2$—N(L$_5$)-, —O—CH$_2$—O—, —O—CH(L$_3$)-O, —S—CH(L$_3$)-O—, —O-L$_3$-, —N-L$_3$-, —S-L$_3$-, —N(L$_3$)-L$_5$- and L$_3$;

L$_4$ is selected from the group consisting of nothing, C=O, C=S,

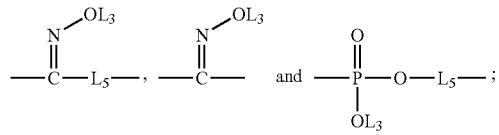

for each L$_2$, and L$_4$, each L$_3$ and L$_5$ is independently selected from the group consisting of nothing, H, CH$_2$C(=O)OL$_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, NL$_3$, or any other pharmaceutically acceptable groups;

L$_6$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)OL$_7$, CH=CH, C≡C, CHL$_7$, CL$_5$L$_7$, aryl, heteroaryl, or cyclic groups; and L$_7$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)OL$_6$, CH=CH, C≡C, CHL$_6$, CL$_6$L$_5$, aryl, heteroaryl, or cyclic groups.

In certain embodiments, a HPP or HPC of a 1H-imidazo[4,5-c]quinolin-4-amine or 1H-imidazo[4,5-c]quinolin-4-amine-related compound comprises the structure of Structure L-1, including stereoisomers and pharmaceutically acceptable salts thereof, wherein:

F, L$_2$, and T are defined as supra; and L$_4$ is —C(=O)—.

Examples of HPPs of
1H-imidazo[4,5-c]quinolin-4-amines and
1H-imidazo[4,5-c]quinolin-4-amine-related
Compounds In certain embodiments, a HPP of a 1H-imidazo[4,5-c]quinolin-4-amine or 1H-imidazo[4,5-c]quinolin-4-amine-related compound includes a compound having a structure selected from the group consisting of Structure P-1, Structure P-2, Structure P-3, Structure P-4, Structure P-5, Structure P-6, Structure P-7, Structure P-8, Structure P-9, Structure P-10, Structure P-11, Structure P-12, Structure P-13, Structure P-14, Structure P-15, Structure P-16, Structure P-17, and Structure P-18:

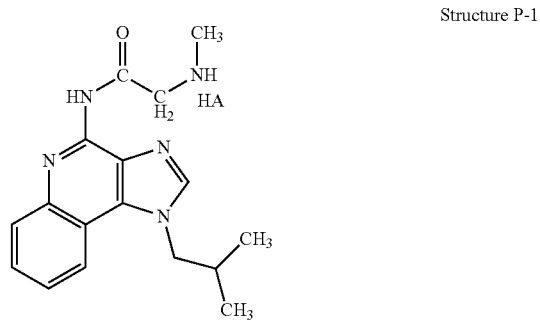

Structure P-1

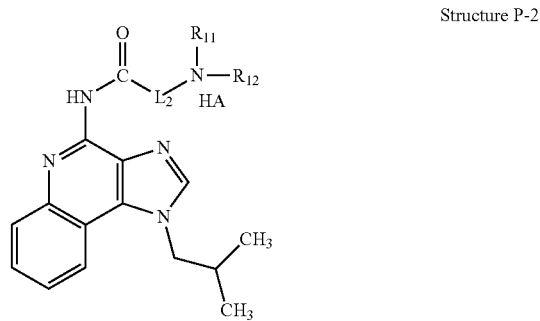

Structure P-2

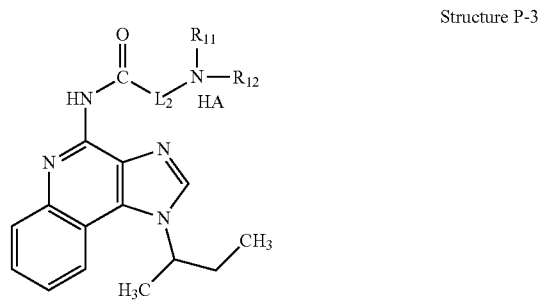

Structure P-3

Structure P-4
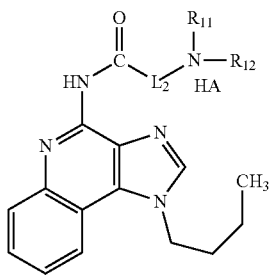
Structure P-5
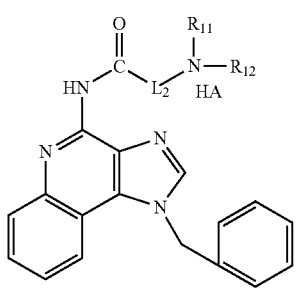
Structure P-6
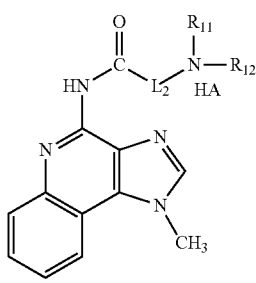
Structure P-7
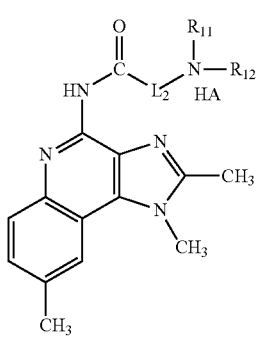
Structure P-8
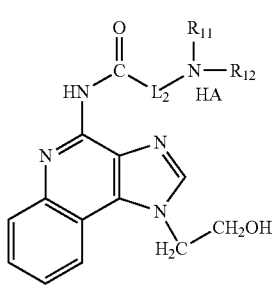
Structure P-9
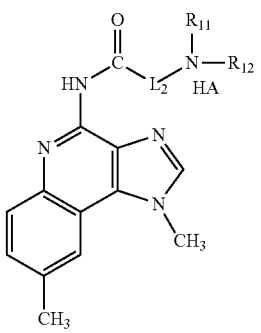
Structure P-10
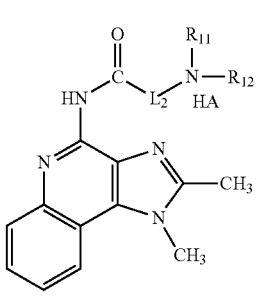
Structure P-11
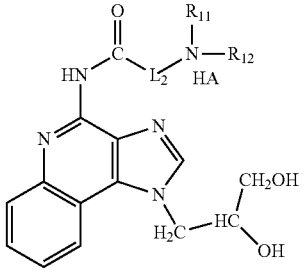
Structure P-12
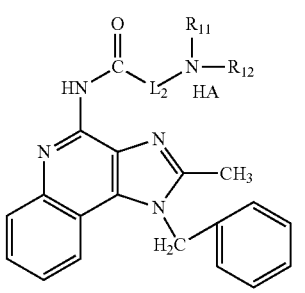
Structure P-13
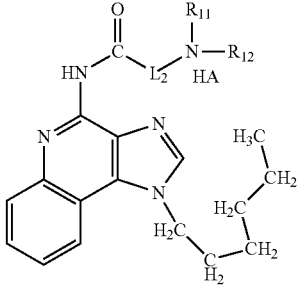

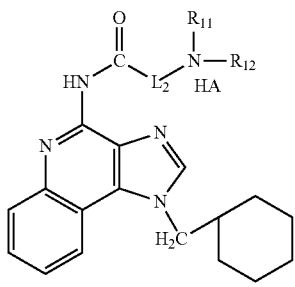

Structure P-14

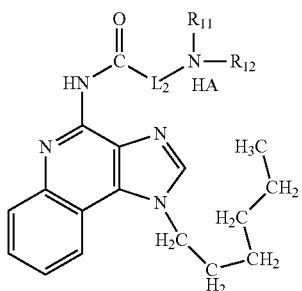

Structure P-15

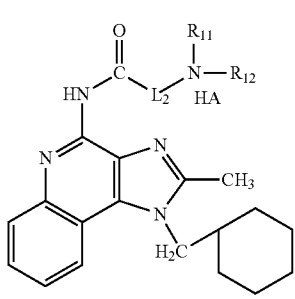

Structure P-16

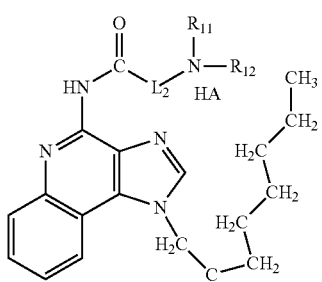

Structure P-17

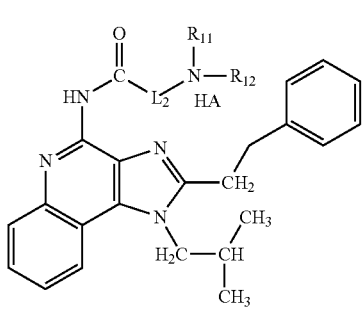

Structure P-18 including stereoisomers and pharmaceutically acceptable salts thereof, wherein:

$L_2$, $R_{11}$ and $R_{12}$ are defined the same as supra; and

HA is nothing or a pharmaceutically acceptable acid, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid or pamoic acid.

II. Pharmaceutical Compositions Comprising HPPs

Another aspect of the invention relates to a pharmaceutical composition comprising at least one HPP of a 1H-imidazo[4,5-c]quinolin-4-amine or 1H-imidazo[4,5-c]quinolin-4-amine-related compound and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPP, of the formulation and suitable for use in contact with the tissue or organ of a biological system without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological system's needs. For example, the concentration can be 0.0001% to 100%, 0.001% to 50%, 0.01% to 30%, 0.1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-10}$ g to about 100 g, about $10^{-10}$ g to about $10^{-3}$ g, about $10^{-9}$ g to about $10^{-6}$ g, about $10^{-6}$ g to about 100 g, about 0.001 g to about 100 g, about 0.01 g to about 10 g, or about 0.01 g to about 1 g per subject per day. Dosages from about 0.01 mg, up to about 5 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

III. Applications of HPPs i) Methods for Penetrating a Biological Barrier.

Another aspect of the invention relates to a method of using a composition of the invention in penetrating one or more biological barriers in a biological subject. The method comprises a step of administering to a biological subject a HPP or a 1H-imidazo[4,5-c]quinolin-4-amine or 1H-imidazo[4,5-c]quinolin-4-amine-related compound, or a pharmaceutical composition thereof. In certain embodiments, a HPP exhibits more than about 5 times or higher, more than about 20 times or higher, 50 times or higher, >about 100 times or higher, >about 200 time higher, >about 300 times or higher, >about 500 times or higher, >about 1,000 times or higher penetration rate through one or more biological barriers than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, and intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract)), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., empidermis). The cells may be normal cells or pathological cells (e.g. disease cells, cancer cells).

Examples of biological structures include structures sealed by tight or occluding junctions which provide a barrier to the entry of toxins, bacteria and viruses, e.g. the blood milk barrier and the blood brain barrier (BBB). In particular, BBB is composed of an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of the inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of the external surface of subjects, organisms, organs or body cavities include capillaries (e.g. capillaries in the heart tissue), mucous membranes that are continuous with skin (e.g. such as at the nostrils, the lips, the ears, the genital area, and the anus), outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani), skin, cuticle (e.g. dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), and a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a demis layer and a subcutaneous layer. The epidermis layer contains several layers including a basal cell layer, a spinous cell layer, a granular cell layer, and a stratum corneum. The cells in the epidermis are called keratinocytes. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Diagnosing a Condition in a Biological System.

Another aspect of the invention relates to a method of using a composition of the invention in diagnosing a condition in a biological system. The method comprises the following steps:

1) administering a composition comprising a HPP of a 1H-imidazo[4,5-c]quinolin-4-amine or 1H-imidazo[4,5-c]quinolin-4-amine-related compound to the biological subject;

2) detecting the presence, location or amount of the HPP, the functional unit of the HPP or a metabolite thereof in the biological subject; and 3) determining a condition in the biological system.

In certain embodiments, the HPP (or the agent cleaved from the HPP) aggregates in the site of action where a condition occurs. In certain embodiments, the presence, location or amount of the functional unit of the HPP is also detected. In certain embodiments, the onset, development, progress, or remission of a condition (e.g., tumor) associated is also determined.

In certain embodiments, the HPP is labeled with or conjugated to a detectable agent. Alternatively, the HPP is prepared to include radioisotopes for detection. Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In certain embodiments, the detectable agent is not necessarily conjugated to the diagnostic agent but is capable of recognizing the presence of the diagnostic agent and the diagnostic agent can be detected.

In certain embodiments, the HPP of the invention can be provided in a kit, i.e., a packaged combination of reagents in predetermined amounts with instructions for performing the diagnostic assay. Where the HPP is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the invention relates to a method of screening a HPP for a desired character.

In certain embodiments, the method comprises:
1) covalently linking a test functional unit to a transportational unit through a linker to form a test composition (or covalently linking a functional unit to a test transportational unit through a linker, or covalently linking a functional unit to a transportational unit through a test linker)
2) administering the test composition to a biological system; and
3) determining whether the test composition has the desired nature or character.

In one embodiment, a desired character may include, for example, 1) the ability of a test functional unit to form a high penetration composition or convert back to a parent drug, 2) the penetration ability and/or rate of a test composition, 3) the efficiency and/or efficacy of a test composition, 4) the transportational ability of a test transportational unit, and 5) the cleavability of a test linker.

iv) Methods for Treating a Condition in a Biological Subject

Another aspect of the invention relates to a method of using a composition of the invention in treating a condition in a biological system. The method comprises administering the pharmaceutical composition to the biological system.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological system," "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means an eukaryotic organism characterized by voluntary movement. Examples of animal include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda), and helminthes (e.g. rotifera).

The term "plant" as used herein means organisms belonging to the kindom Plantae. Examples of plant include, without limitation, seed plants, bryophytes, ferns and fern allies. Examples of seed plants include, without limitation, cycads, ginkgo, conifers, gnetophytes, angiosperms. Examples of bryophytes include, without limitation, liverworts, hornworts and mosses. Examples of ferns include, without limitation, ophioglossales (e.g. adders-tongues, moonworts, and grape-ferns), marattiaceae and leptosporangiate ferns. Examples of fern allies include, without limitation, lycopsida (e.g. club-mosses, spikemosses and quillworts), psilotaceae (e.g. lycopodiophyta and whisk ferns) and equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "micro-organism" as used herein means an organism that is microscopic (e.g. with length scale of micrometer). Examples of micro-organism include, without limitation, bacteria, fungi, archaea, protists and microscopic plants (e.g. green algae) and microscopic animals (e.g. plankton, planarian and amoeba).

Some examples of the conditions the method can treat include conditions that can be treated by the parent drug of the HPP.

v). Methods of using HPPs of 1H-imidazo[4,5-c]quinolin-4-amines and 1H-imidazo[4,5-c]quinolin-4-amine-related Compounds and Pharmaceutical Compositions Thereof in Treatments.

Another aspect of the invention relates to a method of using HPPs of 1H-imidazo[4,5-c]quinolin-4-amines or 1H-imidazo[4,5-c]quinolin-4-amine-related compounds, or pharmaceutical compositions thereof in treating a condition in a biological system or subject by administering a HPP of a 1H-imidazo[4,5-c]quinolin-4-amine or 1H-imidazo[4,5-c]quinolin-4-amine-related compound, or a pharmaceutical composition thereof to the biological system or subject.

1H-imidazo[4,5-c]quinolin-4-amines and 1H-imidazo[4,5-c]quinolin-4-amine-related compounds can be used to regulate a wide range of biological processes in a biological system. Conditions that are related to such biological processes are treatable by the corresponding 1H-imidazo[4,5-c]quinolin-4-amines or 1H-imidazo[4,5-c]quinolin-4-amine-related compounds, and therefore treatable by HPPs/HPCs of the 1H-imidazo[4,5-c]quinolin-4-amines/1H-imidazo[4,5-c]quinolin-4-amine-related compounds, and a pharmaceutical composition thereof.

Without being bounded by any theory, it is believed that 1H-imidazo[4,5-c]quinolin-4-amines are known antiviral agents that are also known to induce interferon biosynthesis (Gerster, J. F., U.S. Pat. No. 4,689,338). The fact that these compounds are interferon inducers suggests that 1H-imidazo[4,5-c]quinolin-4-amines and 1H-imidazo[4,5-c]quinolin-4-amine-related compounds may be useful in the treatment of numerous diseases, such as rheumatoid arthritis, eczema, psoriasis, multiple sclerosis, essential thrombocythaemia, viral diseases and related conditions, and tumor and related conditions. For example, Aldara (1-Isobutyl-1H-imidazo[4,5-c]quinolin-4-amine) cream has been used to treat actinic keratosis, superficial basal cell carcinoma, and external genital and perianal warts.

Conditions that are treatable by HPP/HPC of 1H-imidazo[4,5-c]quinolin-4-amines or 1H-imidazo[4,5-c]quinolin-4-amine-related compounds include, but are not limited to, rheumatoid arthritis, eczema, psoriasis, multiple sclerosis, essential thrombocythaemia, viral diseases and related conditions, and tumor and related conditions.

Examples of viral diseases and related conditions include, without limitation, warts (such as genital and perianal warts, common wart, flat wart, filiform wart, mosaic wart, and any other warts), Actinic Keratosis, flu (such as bird flu(Influenza), swine flu, and any other flu which is caused by influenzavirus A (which includes, but are not limited to H1N1, H2N2, H3N2, H5N1, H7N7, H1N2, H9N2, H7N2, H7N3, H10N7), Influenzavirus B, and/or Influenzavirus C), hepatitis, Severe Acute Respiratory Syndrome (SARS), pneumonia, and acquired immunodeficiency syndrome (AIDS).

Examples of tumor and related conditions include, without limitation, benign tumor, breast cancer, oral cancer, colon-rectum cancer, lung or other respiratory system cancers, skin cancer, superfacial basal cell carcinoma, basal cell carcinoma, cervical cancer, mycosis fungoides, Kaposi's sarcoma, AIDS-related Kaposi's sarcoma, systemic Kaposi's sarcoma, cutaneous T-cell lymphoma (CTCL), squamous cell skin cancer, second primary tumors, head and neck carcinoma, ovarian cancer, prostate cancer, and renal cell cancer.

Some examples of the conditions that are treatable by a method comprising using a HPP/HPC of a 1H-imidazo[4,5-c]quinolin-4-amine or 1H-imidazo[4,5-c]quinolin-4-amine-related compound, or a pharmaceutical composition thereof include, without limitation, rheumatoid arthritis, viral diseases and related conditions, and tumor and related conditions.

In certain embodiments, a method of treating a 1H-imidazo[4,5-c]quinolin-4-amine treatable condition comprises administering to a biological system a HPP/HPC of a 1H-imidazo[4,5-c]quinolin-4-amine or a 1H-imidazo[4,5-c]quinolin-4-amine-related compound such as a compound having a structure selected from the group consisting of Structure A, Structure R1, Structure R2, Structure R3, Structure R4, Structure R5, Structure R6, Structure R7, Structure R8, Structure R9, Structure R10, Structure R11, Structure R12, Structure R13, Structure R14, Structure R15, Structure R16, Structure R17, and Structure R18 as defined supra, and mimics thereof. In certain embodiments, a method of treating a 1H-imidazo[4,5-c]quinolin-4-amine treatable condition comprises administering to a biological system a HPP/HPC of a 1H-imidazo[4,5-c]quinolin-4-amine or a 1H-imidazo[4,5-c]quinolin-4-amine-related compound wherein the HPP/HPC has a structure selected from the group consisting of Structure L-1, Structure P-1, Structure P-2, Structure P-3, Structure P-4, Structure P-5, Structure P-6, Structure P-7, Structure P-8, Structure P-9, Structure P-10, Structure P-11, Structure P-12, Structure P-13, Structure P-14, Structure P-15, Structure P-16, Structure P-17, and Structure P-18 as defined supra, and mimics thereof.

A HPP or a pharmaceutical composition thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

A HPP or a pharmaceutical composition thereof can be given to a subject in the form of formulations or preparations suitable for each administration route. The formulations useful in the methods of the invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPP which can be combined with a carrier material to produce a pharmaceutically effective dose will generally be that amount of a HPP which produces a therapeutic effect. In certain embodiments, out of one hundred percent, the amount of HPP/HPC ranges from about 0.01 percent to about ninety-nine percent of the HPP. In certain embodiments, the amount of HPP/HPC ranges from about 0.1 percent to about 20 percent. In certain embodiments, the amount of HPP/HPC ranges from about 1 percent to about 5 percent.

Methods of preparing these formulations or compositions include the step of bringing into association a HPP with one or more pharmaceutically acceptable carriers and, optionally, one or more accessory ingredients. In general, the formulations are prepared by uniformly and intimately bringing into association a HPP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPP as an active ingredient. A compound may also be administered as a bolus, electuary, or paste.

In solid dosage forms for oral administration (e.g., capsules, tablets, pills, dragees, powders, granules and the like), the HPP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered 1H-imidazo[4,5-c]quinolin-4-amines or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) only, or preferentially, in a certain portion of the gastrointestinal tract, optionally, in a delayed manner. Examples of embedding compositions which can be used include polymeric substances and waxes. The HPP can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

A HPP or a pharmaceutical composition thereof can be alternatively administered by aerosol. This can be accomplished by preparing an aqueous aerosol, liposomal preparation or solid particles containing the HPPs. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to a tumor site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise a HPP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPP or in biodegradable polymers such as polylactide-polyglycolide. Depending on the ratio of the HPP to polymer, and the nature of the particular polymer employed, the rate of drug release can be controlled. Examples of other biodegradable polymers include poly (orthoesters) and poly (anhydrides). Depot injectable formulations are also prepared by entrapping the HPP in liposomes or microemulsions which are compatible with body tissue.

In certain embodiments, a HPP of a 1H-imidazo[4,5-c]quinolin-4-amine or 1H-imidazo[4,5-c]quinolin-4-amine-related compound, or a pharmaceutical composition thereof is delivered to a disease or tumor site in a therapeutically effective dose. As is known in the art of pharmacology, the precise amount of the pharmaceutically effective dose of a HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e.g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins Pa., USA) (2000).

IV. Advantages 1H-imidazo[4,5-c]quinolin-4-amines and 1H-Imidazo[4,5-c]quinolin-4-amine-related compounds often have low solubilities in both inorganic and organic solvents and penetrate the skin membrane barrier very slowly. When 1H-imidazo[4,5-c]quinolin-4-amines are taken orally, 1H-imidazo[4,5-c]quinolin-4-amines and 1H-Imidazo[4,5-c]quinolin-4-amine-related compounds are rapidly metabolizeded by enzymes. In the case of injection, administration of 1H-imidazo[4,5-c]quinolin-4-amines is painful and in many cases requires frequent and costly office visits to treat chronic conditions.

In certain embodiments, since a HPP of the invention is capable of crossing one or more biological barriers, the HPP can be administered locally (e.g., topically or transdermally) to reach a location where a condition occurs without the necessity of a systematic administration (e.g., oral or parenteral administration). A local administration and penetration of a HPP allows the HPP to reach the same level of local concentration of an agent or drug with much less amount or dosage of HPP in comparison to a systematic administration of a parent agent or drug; alternatively, a higher level of local concentration which may not be afforded in the systematic administration, or if possible, requires significantly higher dosage of an agent in the systematic administration. The high local concentration of the HPP or its parent agent if being cleaved enables the treatment of a condition more effectively or much faster than a systematically delivered parent agent and the treatment of new conditions that may not be possible or observed before. The local administration of the HPP may allow a biological subject to reduce potential sufferings from a systemic administration, e.g., adverse reactions associated with the systematic exposure to the agent, gastrointestinal/renal effects. Additionally, the local administration may allow the HPP to cross a plurality of biological barriers and reach systematically through, for example, general circulation and thus avoid the needs for systematic administration (e.g., injection) and obviate the pain associated with the parenteral injection.

In certain embodiments, a HPP or a pharmaceutical composition according to the invention can be administered systematically (e.g., orally or parenterally). The HPP or the active agent (e.g., drug or metabolite) of the HPP may enter the general circulation with a faster rate than the parent agent and gain faster access to the action site a condition. Additionally, the HPP can cross a biological barrier (e.g., blood brain barrier) which has not been penetrated if a parent agent is administered alone and thus offer novel treatment of conditions that may not be possible or observed before.

For example, HPPs of 1H-imidazo[4,5-c]quinolin-4-amines or 1H-imidazo[4,5-c]quinolin-4-amine-related compounds in the invention demonstrated high penetration rate through a biological barrier (e.g., >about 5 times, >about 25 times, >about 50 times, >about 100 times, >about 200 times, >about 300 times, >about 1000 times higher than if the 1H-imidazo[4,5-c]quinolin-4-amines or 1H-imidazo[4,5-c]quinolin-4-amine-related compounds are administered alone). No or few adverse side effect was observed from the subjects that took 1H-imidazo[4,5-c]quinolin-4-amines HPP, while side effects (such as redness, swelling, sores, blisters, or ulcers, skin that becomes hard or thickened, skin peeling, scabbing and crusting, itching, burning and changes in skin color) were observed from the subjects that took the parent 1H-imidazo[4,5-c]quinolin-4-amines at the similar dosage.

V. EXAMPLES

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

Preparation of a HPP from a Parent Drug

Preparation of a HPP from a Parent Drug which Contains at Least One Carboxylic group.

In certain embodiments, a parent compound having Structure F—C:

    Structure F—C is converted to a HPP having Structure L-1:

    Structure L-1 including stereoisomers and pharmaceutically acceptable salts thereof, wherein:

F, $L_2$, and $L_4$ are defined as supra;

T is a transportational unit of a HPP of a 1H-imidazo[4,5-c]quinolin-4-amine or 1H-imidazo[4,5-c]quinolin-4-amine-related compound. For example, T is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra.

In certain embodiments of the invention, a parent compound having Structure F—C is prepared using the methods disclosed in U.S. Pat. No. 4,689,388, which is incorporated herein by reference in its entirety. A HPP having Structure L-1 is prepared according to organic synthesis by reacting the parent compounds with compounds of Structure E (Scheme 1):

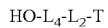    Structure E

F, $L_2$, $L_4$, and T are defined as supra, and the amine group in T may be protected

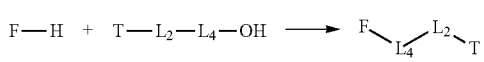

Scheme 1. Preparation of a HPP from a Parent Compound (I).

In certain embodiments, a HPP having Structure L-1 is prepared following Scheme 1 as described supra, wherein $L_4$ is C=O.

In certain embodiments, a preparation of a HPP/HPC of a 1H-imidazo[4,5-c]quinolin-4-amine or 1H-imidazo[4,5-c]quinolin-4-amine-related compound as described supra also uses coupling reagents, such as N,N'-Dicyclohexylcarbodiimide, N, N'-Diisopropylcarbodiimide, O-(Benzotriazol-1-yl)-N,N,N',N'-tetramethyluronium tetrafluoroborate, O-(Benzotriazol-1-yl)-N,N,N',N'-tetramethyluronium hexafluorophosphate, Benzotriazol-1-yl-oxy-tris(dimethylamino)phosphonium hexafluorophosphate.

In certain embodiments of the invention, a HPP/HPC of a 1H-imidazo[4,5-c]quinolin-4-amine or 1H-imidazo[4,5-c]quinolin-4-amine-related compound having Structure L-1 is prepared according to organic synthesis by reacting a parent compound having Structure F-C with a compound having the following Structure 2 (Scheme 2):

    Structure 2

Structure 2 wherein, Z is selected from the group consisting of halogen, F, Cl, Br, I, $R_{20}O—C(=O)—O—$, $R_{20}—C(=O)—O—$, p-toluenesulphonyl, and $T-L_2-L_4-O$ wherein the amine group in T may be protected;

$R_{20}$ is selected from the group consisting of substituted and unsubstituted alkyl, and substituted and unsubstituted aryl; and $L_4$, $L_2$, HA, and T are defined the same as supra.

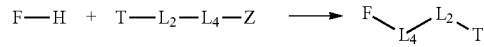

Scheme 2. Preparation of a HPP from a Parent Compound (II).

In certain embodiments, a HPP having Structure L-1 is prepared following Scheme 2 as described supra, wherein $L_4$ is C=O.

Preparation of Boc-sarcosine 1-isobutyl-1H-imidazo[4,5-c]quinolin-4-amide 32.2 g (0.1 mol) of 1-isobutyl-1H-imidazo[4,5-c]quinolin-4-amine was suspended in 500 ml of ethyl acetate. 72 g (0.2 mol) of N-t-Butyloxycarbonyl-N-methylglycine anhydride [(Boc-N-Me-Gly)$_2$O] and 30 ml of triethylamine were added into the reaction mixture. The mixture was refluxed for 8 h. The solution was washed with water (1×100 ml), 10% citric acid (1×100 ml), water (1×100 ml), 5% sodium bicarbonate (1×100 ml), and water (3×100 ml). The ethyl acetate solution was dried over anhydrous sodium sulfate. The ethyl acetate solution was evaporated to dryness. After drying, it yielded 36 g of the desired product (87.5%). Elementary analysis: $C_{22}H_{29}N_5O_3$; MW: 411.50; calculated % C, 64.21; H, 7.10; N, 17.02; O: 11.66. found % C, 64.17; H, 7.15; N, 16.97; O: 11.71.

Preparation of Sarcosine 1-isobutyl-1H-imidazo[4,5-c]quinolin-4-amide Hydrochloride 35 g of Boc-sarcosine 1-isobutyl-1H-imidazo[4,5-c]quinolin-4-amide was dissolved in ethanol (200 ml). HCl gas was bubbled into the reaction mixture for 20 min. slowly. The mixture was stirred for 1 hour at RT. Ether (300 ml) was added into the mixture. The solid was collected by filtration and washed with ether (3×). After drying, it yielded 27 g of the desired product (91.2%). Elementary analysis: $C_{17}H_{22}ClN_5O$; MW: 347.84; calculated % C, 58.70; H, 6.37; Cl: 10.19; N, 20.13; O: 4.60. found % C, 58.67; H, 6.41; Cl: 10.17; N, 20.11; O: 4.64.

Preparation of Boc-Glycine 1-butyl-1H-imidazo[4,5-c]quinolin-4-amide 32.2 g (0.1 mol) of 1-butyl-1H-imidazo[4,5-c]quinolin-4-amine was suspended in 300 ml of ethyl acetate. 67 g (0.2 mol) of N-t-Butyloxycarbonyl-glycine anhydride (Boc-N-Gly)$_2$O and 30 ml of triethylamine were added into the reaction mixture. The mixture was refluxed for 8 h. The solution was washed with water (1×100 ml), 10% citric acid (1×100 ml), water (1×100 ml), 5% sodium bicarbonate (1×100 ml), and water (3×100 ml). The ethyl acetate solution was dried over anhydrous sodium sulfate. The ethyl acetate solution was evaporated to dryness. After drying, it yielded 37 g of the desired product (93.1%). Elementary analysis: $C_{21}H_{27}N_5O_3$; MW: 397.47; calculated % C, 63.46; H, 6.85; N, 17.62; O: 12.08. found % C, 63.42; H, 6.87; N, 17.60; O: 12.11.

Preparation of glycine 1-isobutyl-1H-imidazo[4,5-c]quinolin-4-amide hydrochloride 36 g of Boc-glycine 1-isobutyl-1H-imidazo[4,5-c]quinolin-4-amide was dissolved in ethanol (200 ml). HCl gas was bubbled into the reaction mixture for 20 min. slowly. The mixture was stirred for 1 hour at RT. Ether (300 ml) was added into the mixture. The solid was collected by filtration and washed with ether (3×). After drying, it yielded 28 g of the desired product (92.6%). Elementary analysis: $C_{16}H_{20}ClN_5O$; MW: 333.82; calculated % C, 57.57; H, 6.04; Cl: 10.62; N, 20.98; O: 4.79. found % C, 57.52; H, 6.08; Cl: 10.67; N, 20.95; O: 4.78.

Preparation of N,N-dimethylglycine 1-butyl-1H-imidazo[4,5-c]quinolin-4-amide Hydrochloride Glycine 1-butyl-1H-imidazo[4,5-c]quinolin-4-amide hydrochloride (27 g) was dissolved in 2N NaOH (50 ml). 50 ml of 40% formaldehyde and 50 ml of acetic acid were added into the reaction mixture. 30 g of NaBH$_4$ was added into the reaction mixture slowly. After addition, the mixture was stirred for 30 min. Another 25 ml of 40% formaldehyde and 10 ml of acetic acid was added into the reaction mixture. 20 g of NaBH$_4$ was added into the reaction mixture slowly. The mixture was evaporated to dryness. The residue was purified by silica gel column chromatography. Yielded 20 g of desired product (68.8%). Elementary analysis: $C_{18}H_{24}ClN_5O$; MW: 361.87; calculated % C, 59.74; H, 6.68; Cl: 9.80; N, 19.35; O: 4.42. found % C, 59.72; H, 6.72; Cl: 9.75; N, 19.37; O: 4.44.

Preparation of Boc-sarcosine 1-benzyl-1H-imidazo[4,5-c]quinolin-4-amide 18.9 g (0.1 mol) of N-t-Butyloxycarbonyl-N-methylglycine was dissolved in 300 ml of dichloromethylene. 20.6 g of N,N'-Dicyclohexylcarbodiimide was added into the reaction mixture. The mixture was stirred for 1 hour at 0° C. 32.2 g (0.1 mol) of 1-benzyl-1H-imidazo[4,5-c]quinolin-4-amine and 20 ml of triethylamine were added into the reaction mixture. The mixture was stirred for 3 hours at RT. The solid was removed by filtration. The dichloromethylene solution was washed with water (1×100 ml), 30% citric acid (1×100 ml), water (1×100 ml), 5% NaHCO$_3$ (2×100 ml), and water (3×100 ml). The organic solution was dried over anhydrous sodium sulfate. Sodium sulfate was removed by filtration. The organic solution was evaporated to dryness. After drying, it yielded 33 g of the desired product (74.1%). Elementary analysis: $C_{25}H_{27}N_5O_3$; MW: 445.51; calculated % C, 67.40; H, 6.11; N, 15.72; O: 10.77. found % C, 67.35; H, 6.14; N, 15.70; O: 10.81.

Preparation of sarcosine 1-benzyl-1H-imidazo[4,5-c]quinolin-4-amide hydrochloride 32 g of Boc-sarcosine 1-benzyl-1H-imidazo[4,5-c]quinolin-4-amide was dissolved in ethanol (200 ml). HCl gas was bubbled into the reaction mixture for 20 min. slowly. The mixture was stirred for 1 hour at RT. Ether (300 ml) was added into the mixture. The solid was collected by filtration and washed with ether (3×). After drying, it yielded 25 g of the desired product (85.7%). Elementary analysis: $C_{20}H_{20}ClN_5O$; MW: 381.86; calculated % C, 62.91; H, 5.28; Cl: 9.28; N, 18.34; O: 4.19. found % C, 62.87; H, 5.31; Cl: 9.30; N, 18.32; O: 4.20.

Example 2

HPPs of 1H-imidazo[4,5-c]quinolin-4-amines and 1H-imidazo[4,5-c]quinolin-4-amine-related Compounds have Higher In Vitro Penetration Rates Across Human Skin Comparing to their Parent Drugs Penetration rates of HPPs and their parent drugs through human skin were measured in vitro by modified Franz cells. A Franz cell had two chambers, the top sample chamber and the bottom receiving chamber. The human skin tissue (360-400 μm thick) that separated the top and the receiving chambers was isolated from the anterior or posterior thigh areas.

A compound tested (0.5 mL, 3% in a mixture of ethanol and phosphate buffer (0.2M, pH 7.4) (v/v, 70/30)) was added to the sample chamber of a Franz cell. The receiving chamber contains 2 ml of 2% bovine serum albumin in saline which was stirred at 600 rpm. The amount of the tested compound penetrating the skin was determined by high-performance liquid chromatography (HPLC) method. The results were shown in FIG. 1. The apparent flux values of the tested compounds were calculated from the slopes in the FIG. 1 and summarized in Tables 1.

The lowest detectable apparent flux values in this method was 1 μg/cm$^2$/h. The HPPs of 1H-imidazo[4,5-c]quinolin-4-amines or 1H-imidazo[4,5-c]quinolin-4-amine-related compounds showed a higher (25 times higher) penetration rate across the skin tissue comparing to their parent compounds.

TABLE 1

In vitro Penetration Rate of HPPs and their Parent Compounds

| HPPs | mg/cm$^2$/h | Parent compounds | mg/cm$^2$/h |
|---|---|---|---|
| sarcosine 1-isobutyl-1H-imidazo[4,5-c]quinolin-4-amide hydrochloride | 0.15 | 1-isobutyl-1H-imidazo[4,5-c]quinolin-4-amine hydrochloride | 0.005 |
| sarcosine 1-butyl-1H-imidazo[4,5-c]quinolin-4-amide hydrochloride | 0.13 | 1-butyl-1H-imidazo[4,5-c]quinolin-4-amine hydrochloride | 0.005 |
| sarcosine 1-benzyl-1H-imidazo[4,5-c]quinolin-4-amide hydrochloride | 0.16 | 1-benzyl-1H-imidazo[4,5-c]quinolin-4-amine hydrochloride | 0.005 |

Example 3

Irritative Effect or Discomfort of HPPs of 1H-imidazo[4,5-c]quinolin-4-amines and 1H-imidazo[4,5-c]quinolin-4-amine-related Compounds on Skin of Mice Irritative effect or discomfort in the skin of mice of HPPs of 1H-imidazo[4,5-c]quinolin-4-amines or 1H-imidazo[4,5-c]quinolin-4-amine-related compounds was evaluated during a period of 1 week after the topical application of 0.1 ml of 3% of the respective test drug in pH 7.4 phosphate buffer (0.2 M) to the back of nude mice twice per day. None of any signs of irritative effect or discomfort was observed for sarcosine 1-isobutyl-1H-imidazo[4,5-c]quinolin-4-amide hydrochloride, sarcosine 1-butyl-1H-imidazo[4,5-c]quinolin-4-amide hydrochloride, sarcosine 1-benzyl-1H-imidazo[4,5-c]quinolin-4-amide hydrochloride.

Example 4

Conversion of HPPs of 1H-imidazo[4,5-c]quinolin-4-amines and 1H-imidazo[4,5-c]quinolin-4-amine-related Compounds to their Parent Drugs HPPs of 1H-imidazo[4,5-c]quinolin-4-amines or 1H-imidazo[4,5-c]quinolin-4-amine-related compounds converted to the parent 1H-imidazo[4,5-c]quinolin-4-amines or 1H-imidazo[4,5-c]quinolin-4-amine-related compounds quickly in good yield in human plasma.

A HPP of 1H-imidazo[4,5-c]quinolin-4-amines or 1H-imidazo[4,5-c]quinolin-4-amine-related compound (0.05 mg) was dissolved in 0.1 ml of 0.2M pH 7.4 phosphate buffer. 1 ml of human plasma, preheated to 37° C., was added into the mixture. The mixture was kept in a water bath at 37° C., and at every 10 min intervals 0.2 ml of samples were withdrawn and added to 0.4 ml of methanol to precipitate the plasma protein. The samples were centrifuged for 5 min and analyzed by HPLC. The results showed the half-lives of the HPPs of 1H-imidazo[4,5-c]quinolin-4-amines or 1H-imidazo[4,5-c]quinolin-4-amine-related compounds were converted back to the parent 1H-imidazo[4,5-c]quinolin-4-amines or 1H-imidazo[4,5-c]quinolin-4-amine-related compounds (Table 2).

TABLE 2

Half life of HPPs in plasma

| HPP | Half life (min) |
| --- | --- |
| sarcosine 1-isobutyl-1H-imidazo[4,5-c]quinolin-4-amide hydrochloride | 27 +/− 1 |
| sarcosine 1-butyl-1H-imidazo[4,5-c]quinolin-4-amide hydrochloride | 25 +/− 2 |
| sarcosine 1-benzyl-1H-imidazo[4,5-c]quinolin-4-amide hydrochloride | 29 +/− 1 |

Example 5

Antitumor Activity of HPPs of 1H-imidazo[4,5-c]quinolin-4-amines and 1H-imidazo[4,5-c]quinolin-4-amine-related Compounds (I)

Human breast cancer cells (BCAP-37, 4-5 mm$^3$ of tumor tissue was used in each mouse) were subcutaneous xenografted into nude mice (BALB). After 1 day, the mice were divided into three groups: HPP group, parent drug group and control group which were treated topically at the human breast cancer cells-implanted area (near the front leg) with 50 μl of 3% of sarcosine 1-isobutyl-1H-imidazo[4,5-c]quinolin-4-amide hydrochloride, 50 μl of 3% of 1-isobutyl-1H-imidazo[4,5-c]quinolin-4-amine hydrochloride in ethanol/0.2M pH 7.2 phosphate buffer (v/v, 70/30), and 50 μl of a mixture of ethanol/0.2M pH 7.2 phosphate buffer (v/v, 70/30) once per day respectively. After 28 days, the control group and the parent drug group demonstrated 100% incidence, but no tumor was seen in the HPP group (Table 3). The average weights of the mice were not significantly different among the three group (Table 3), which showed that the prodrug had very mild side effects.

Human colon cancer cells (LS174J, 4-5 mm$^3$ of tumor tissue was used in each mouse) were subcutaneously xenografted into nude mice (BALB). After 1 day, the mice were divided into three groups: HPP group, parent drug group and control group which were treated topically at the human breast cancer cells-implanted area (near the front leg) with 50 μl of 3% of sarcosine 1-isobutyl-1H-imidazo[4,5-c]quinolin-4-amide hydrochloride, 50 μl of 3% of 1-isobutyl-1H-imidazo[4,5-c]quinolin-4-amine hydrochloride in ethanol/0.2M pH 7.2 phosphate buffer (v/v, 70/30), and 50 μl of a mixture of ethanol/0.2M pH 7.2 phosphate buffer (v/v, 70/30) twice per day respectively. After 28 days, the control group and the parent drug group demonstrated 100% incidence, but no tumor was seen in the HPP group (Table 3). The average weights of the mice were not significantly different among the three groups (Table 3), which showed that the prodrug had very mild side effects.

TABLE 3

Summary of antitumor activity of HPP of 1H-imidazo[4,5-c]quinolin-4-amine

| | | Human breast cancer | | Human colon cancer | |
| --- | --- | --- | --- | --- | --- |
| | Treated with | Tumor size | Average weight (g) | Tumor size | Average weight (g) |
| HPP group | sarcosine 1-isobutyl-1H-imidazo[4,5-c]quinolin-4-amide hydrochloride | None | 22 ± 2 | None | 21 ± 2 |
| Parent drug group | 1-isobutyl-1H-imidazo[4,5-c]quinolin-4-amine hydrochloride | 12 ± 2 mm × 11 ± 2 mm | 22 ± 2 | 17 ± 2 mm × 15 ± 2 mm | 21 ± 2 |
| Control group | 50 μl of a mixture of ethanol/0.2M pH 7.2 phosphate buffer (v/v, 70/30) | 15 ± 2 mm × 13 ± 2 mm | 24 ± 2 | 20 ± 3 mm × 18 ± 3 mm | 23 ± 2 |

Example 6

Antitumor Activity of HPPs of 1H-imidazo[4,5-c]quinolin-4-amines and 1H-imidazo[4,5-c]quinolin-4-amine-related Compounds (II)

Human breast cancer cells (BCAP-37, 3-4 mm$^3$ of tumor tissue was used in each mouse) were subcutaneously xenografted into nude mice (BALB). After 21 days, the tumors grew to the size of 13±2 mm×12±3 mm. The mice were divided into three groups: HPP group, parent drug group and control group which were treated topically at the human breast cancer cells-implanted area (near the front leg) with 50 µl of 3% of sarcosine 1-isobutyl-1H-imidazo[4,5-c]quinolin-4-amide hydrochloride, 50 µl of 3% of 1-isobutyl-1H-imidazo[4,5-c]quinolin-4-amine hydrochloride in ethanol/0.2M pH 7.2 phosphate buffer (v/v, 70/30), and 50 µl of a mixture of ethanol/0.2M pH 7.2 phosphate buffer (v/v, 70/30) once per day respectively. At day 42, the tumors grew to the size of 21±3 mm×19±3 mm in the control group and all mice died by day 60. In the parent drug group, the tumors were 17±2 mm×15±2 mm and all mice died by day 70. The tumors in the HPP group shrunk to 11±2 mm×10±2 mm and none of mice died at day 70. The average weights of the mice were 21±2 grams for the HPP group, 22±2 grams for parent drug group, and 23±2 grams for the control group at day 45.

Example 7

Interferon Inducing Activity of HPPs of 1H-imidazo[4,5-c]quinolin-4-amines

Without being bound by any mechanism, the ability to induce interferon production of the pro-drugs of the invention was evaluated in guinea pigs (n=10). Untreated guinea pigs provided controls.

Sarcosine 1-isobutyl-1H-imidazo[4,5-c]quinolin-4-amide hydrochloride and N,N-dimethylglycine 1-n-hexyl-1H-imidazo[4,5-c]quinolin-4-amide hydrochloride were administered as solution in ethanol/0.2M pH 7.2 phosphate buffer (v/v, 70/30), and 1-isobutyl-1H-imidazo[4,5-c]quinolin-4-amine hydrochloride and 1-hexyl-1H-imidazo[4,5-c]quinolin-4-amine hydrochloride were administered as suspension in ethanol/0.2M pH 7.2 phosphate buffer (v/v, 70/30).

Each test drug (Sarcosine 1-isobutyl-1H-imidazo[4,5-c]quinolin-4-amide hydrochloride, N,N-dimethylglycine 1-n-hexyl-1H-imidazo[4,5-c]quinolin-4-amide hydrochloride, 1-isobutyl-1H-imidazo[4,5-c]quinolin-4-amine hydrochloride and 1-hexyl-1H-imidazo[4,5-c]quinolin-4-amine hydrochloride) was administered once intravaginally to guinea pigs at a specific dose of about 0.5-4.5 mg/k respectively.

Each test drug was administered to real back skin of a guinea pig at a specific dose of about 0.5-4.5 mg/kg respectively.

Each treated and control guinea pig was bled 18 hours after drug treatment and its serum was assayed for interferon activity. The serum was diluted and incubated with guinea pig fibroblast cells at 37° C. overnight in 96 well microtiter plates. The incubated cells were then challenged with an inoculum of mengovirus that was sufficient to kill untreated cells in two days. Two days after such challenge, the cells were examined both microscopically and after staining with crystal violet to determine whether the cells remained intact.

Table 4 contains the results of the study with activity/ml indicating the highest dilute on of serum that protected cells from virus challenge. Untreated guinea pigs provided controls. HPPs showed higher ability to induce interferon production in guinea pigs than their respective parent drugs.

TABLE 4

The ability to induce interferon production of 1H-imidazo[4,5-c]quinolin-4-amines and their HPPs by intravaginal administration and transdermal administration.

| HPP | Dosage (mg/kg) | Interferon level of the parent drug (activity/ml) | | Interferon level of the HPP (activity/ml) | |
|---|---|---|---|---|---|
| | | intra-vaginal | trans-dermal | intra-vaginal | trans-dermal |
| Sarcosine 1-isobutyl-1H-imidazo[4,5-c]quinolin-4-amide hydrochloride | 0.5 | 385 | 198 | 23,647 | 8,676 |
| | 1.5 | 2,982 | 776 | 56,735 | 16,784 |
| | 4.5 | 28,982 | 2,785 | 87,795 | 57,235 |
| N,N-dimethylglycine 1-n-hexyl-1H-imidazo[4,5-c]quinolin-4-amide hydrochloride | 0.5 | 286 | 178 | 21,857 | 11,756 |
| | 1.5 | 1,562 | 565 | 57,147 | 22,537 |
| | 4.5 | 24,786 | 1,945 | 78,569 | 61,758 |
| Control group | 0 | <100 | <100 | <100 | <100 |

Example 8

Anti-Herpes Activity of HPPs of 1H-imidazo[4,5-c]quinolin-4-amines

The evaluation of anti-Herpes activity of these prodrugs was carried out using the method described by Kern, et al. [Antimicrob. Agents Chemother. 14, 817, (1978)].

In each experiment, female guinea pigs (n=10) were anesthetized. Sarcosine 1-isobutyl-1H-imidazo[4,5-c]quinolin-4-amide hydrochloride and N,N-dimethylglycine 1-n-hexyl-1H-imidazo[4,5-c]quinolin-4-amide hydrochloride were administered as solution in ethanol/0.2M pH 7.2 phosphate buffer (v/v, 70/30), and 1-isobutyl-1H-imidazo[4,5-c]quinolin-4-amine hydrochloride and 1-hexyl-1H-imidazo[4,5-c]quinolin-4-amine hydrochloride were administered as suspension in in ethanol/0.2M pH 7.2 phosphate buffer (v/v, 70/30).

In the first experiment, each test drug was administered once per day intravaginally or transdermally (to the real back skin) to an uninfected guinea pig at a specific dose of about 0.5-4.5 mg/kg for 3 days. The guinea pigs were then infected with herpes simplex virus (Type I or Type II, about 10$^5$ plaque forming units was used) intravaginally using a cotton swab. Virus replication was monitored by determining the amount of virus recovered with vaginal swabs taken on day 7 after infection. External lesions were scored daily for ten days using the following scale: 0, no lesion; 1, redness and swelling; 2, a few small vesicles; 3, several large vesicles; 4, large ulcers and necrosis; and 5, paralysis. The percent Lesion Inhibition was calculated as follows: 100−[(Sum of maximum lesion scores of treated group divided by the Sum of the scores of infected control)×100] (Table 5).

TABLE 5

Anti-Herpes activity of 1H-imidazo[4,5-c]quinolin-4-amines and their HPPs by intravaginal and transdermal administration (treated for 3 days before HSV infection).

| HPP | Dosage (mg/kg) | % Lesion inhibition of the parent drug | | | | % Lesion inhibition of the HPP | | | |
|---|---|---|---|---|---|---|---|---|---|
| | | intravaginal | | transdermal | | intravaginal | | transdermal | |
| | | \multicolumn{8}{c}{Herpes type} | | | | | | | |
| | | I | II | I | II | I | II | I | II |
| Sarcosine 1-isobutyl-1H-imidazo[4,5-c]quinolin-4-amide hydrochloride | 0.5 | 4 | 5 | 2 | 2 | 71 | 75 | 45 | 51 |
| | 1.5 | 23 | 28 | 3 | 2 | 93 | 90 | 72 | 73 |
| | 4.5 | 85 | 87 | 45 | 48 | 95 | 96 | 91 | 90 |
| N,N-dimethylglycine 1-n-hexyl-1H-imidazo[4,5-c]quinolin-4-amide hydrochloride | 0.5 | 4 | 5 | 2 | 2 | 67 | 68 | 38 | 40 |
| | 1.5 | 16 | 18 | 3 | 3 | 91 | 90 | 67 | 68 |
| | 4.5 | 80 | 81 | 42 | 45 | 95 | 95 | 91 | 93 |
| Control group | 0 | — | — | — | — | — | — | — | — |

In the second experiment, female guinea pigs (n=10) were anesthetized. Herpes simplex virus (Type I or Type II, about $10^5$ plaque forming units were used) was applied intravaginally to the guinea pigs using a cotton swab. Then each test drug (sarcosine 1-isobutyl-1H-imidazo[4,5-c]quinolin-4-amide hydrochloride, N,N-dimethylglycine 1-n-hexyl-1H-imidazo[4,5-c]quinolin-4-amide hydrochloride, 1-isobutyl-1H-imidazo[4,5-c]quinolin-4-amine hydrochloride and 1-hexyl-1H-imidazo[4,5-c]quinolin-4-amine hydrochloride) was administered once per day intravaginally or transdermally (to the real back skin) to an infected guinea pig at a specific dose of about 0.5-5 mg/kg for 5 days respectively. Virus replication was monitored by determining the amount of virus recovered with vaginal swabs taken on day 7 after infection. External lesions were scored daily for ten days using the following scale: 0, no lesion; 1, redness and swelling; 2, a few small vesicles; 3, several large vesicles; 4, large ulcers and necrosis; and 5, paralysis. The percent Lesion Inhibition was calculated as follows: 100−[(Sum of maximum lesion scores of treated group divided by the Sum of the scores of infected control)×100] (Table 6).

In the third experiment, female guinea pigs (n=10) were anesthetized. The guinea pigs were then infected with herpes simplex virus (type I or Type II, about $10^5$ plaque forming units were used) intravaginally using a cotton swab. After 5 days, each test drug (sarcosine 1-isobutyl-1H-imidazo[4,5-c]quinolin-4-amide hydrochloride, N,N-dimethylglycine 1-n-hexyl-1H-imidazo[4,5-c]quinolin-4-amide hydrochloride, 1-isobutyl-1H-imidazo[4,5-c]quinolin-4-amine hydrochloride and 1-hexyl-1H-imidazo[4,5-c]quinolin-4-amine hydrochloride) was administered once per day intravaginally or transdermally to the rear back skin to an infected guinea pig at a specific dose of about 0.5-5 mg/kg respectively for 5 days. External lesions were scored daily for ten days using the following scale: 0, no lesion; 1, redness and swelling; 2, a few small vesicles; 3, several large vesicles; 4, large ulcers and necrosis; and 5, paralysis. The percent Lesion Inhibition was calculated as follows: 100−[(Sum of maximum lesion scores of treated group divided by the Sum of the scores of infected control)×100] (Table 7).

TABLE 6

Anti-Herpes activity of 1H-imidazo[4,5-c]quinolin-4-amines and their HPPs by intravaginal and transdermal administration (treated for 5 days and the first treatment just after HSV infection).

| HPP | Dosage (mg/kg) | % Lesion inhibition of the Parent Drug | | | | % Lesion inhibition of the HPP | | | |
|---|---|---|---|---|---|---|---|---|---|
| | | intravaginal | | transdermal | | intravaginal | | transdermal | |
| | | \multicolumn{8}{c}{Herpes type} | | | | | | | |
| | | I | II | I | II | I | II | I | II |
| Sarcosine 1-isobutyl-1H-imidazo[4,5-c]quinolin-4-amide hydrochloride | 0.5 | 2 | 2 | 2 | 2 | 57 | 56 | 47 | 49 |
| | 1.5 | 17 | 21 | 7 | 6 | 87 | 90 | 77 | 80 |
| | 4.5 | 78 | 82 | 52 | 54 | 95 | 96 | 91 | 93 |
| N,N-dimethylglycine 1-n-hexyl-1H-imidazo[4,5-c]quinolin-4-amide hydrochloride | 0.5 | 2 | 2 | 2 | 2 | 67 | 68 | 37 | 38 |
| | 1.5 | 11 | 11 | 5 | 6 | 91 | 90 | 73 | 75 |
| | 4.5 | 68 | 71 | 43 | 41 | 95 | 95 | 90 | 91 |
| Control group | 0 | — | — | — | — | — | — | — | — |

TABLE 7

The anti-Herpes activity of 1H-imidazo[4,5-c]quinolin-4-amines and their HPPs by intravaginal and transdermal administration (treated for 5 days and the first treatment started 5 days after HSV infection).

| HPP | Dosage (mg/kg) | % Lesion inhibition of the parent drug | | | | % Lesion inhibition of the HPP | | | |
|---|---|---|---|---|---|---|---|---|---|
| | | intravaginal | | transdermal | | intravaginal | | transdermal | |
| | | Herpes type | | | | | | | |
| | | I | II | I | II | I | II | I | II |
| Sarcosine 1-isobutyl-1H-imidazo[4,5-c]quinolin-4-amide hydrochloride | 0.5 | 2 | 2 | 2 | 2 | 37 | 38 | 37 | 38 |
| | 1.5 | 2 | 2 | 2 | 2 | 68 | 70 | 57 | 58 |
| | 4.5 | 37 | 44 | 22 | 24 | 88 | 90 | 89 | 88 |
| N,N-dimethylglycine 1-n-hexyl-1H-imidazo[4,5-c]quinolin-4-amide hydrochloride | 0.5 | 2 | 2 | 2 | 2 | 31 | 28 | 28 | 25 |
| | 1.5 | 2 | 2 | 2 | 2 | 62 | 65 | 52 | 55 |
| | 4.5 | 35 | 37 | 18 | 21 | 83 | 85 | 82 | 81 |
| Control group | 0 | — | — | — | — | — | — | — | — |

The results showed that the HPPs of 1H-imidazo[4,5-c]quinolin-4-amines or 1H-imidazo[4,5-c]quinolin-4-amine-related compounds had stronger anti-herpes simplex virus activities than their respective parent drugs when they were administered, intravaginally and transdermally, to guinea pigs before, at the same time, or after infection.

Example 9

Treatment of Breast Cancer using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to the skin on the tumor twice per day. The process is repeated until the tumor disappears. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 10

Treatment of Breast Cancer after Cancer Removal Surgery Using HPPs of 1H-imidazo[4,5-c]quinolin-4-amines or 1H-imidazo[4,5-c]quinolin-4-amine-related Compounds 3 days after tumor is removed, 1 ml of 2% sarcosine 1-isobutyl-1H-imidazo[4,5-c]quinolin-4-amide hydrochloride in 70% ethanol is sprayed to any skin surface of the body twice per day. The process is repeated for 3 months or until tumor disappears. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 11

Treatment of Breast Cancer Before an after Cancer Removal Surgery using HPPs of 1H-imidazo[4,5-c]quinolin-4-amines or 1H-imidazo[4,5-c]quinolin-4-amine-related Compounds Before the surgery, 1 ml of 2% sarcosine 1-isobutyl-1H-imidazo[4,5-c]quinolin-4-amide hydrochloride in 70% ethanol is sprayed to the skin on the tumor twice per day. 3 days before and 3 days after the surgery, the treatment is stopped. 3 days after tumor is removed, 1 ml of 2% sarcosine 1-isobutyl-1H-imidazo[4,5-c]quinolin-4-amide hydrochloride in 70% ethanol is sprayed to the around the tumor site or any skin surface of the body twice per day. The process is repeated for 3 months or until tumor does not show up for 3 months. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 12

Treatment of Prostate Cancer using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to the skin on the tumor (the pubic area) twice per day. The process is repeated until the tumor disappears. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 13

Treatment of Lung Cancer using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to the skin on the chest twice per day. The process is repeated until the tumor disappears. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 14

Treatment of Lung Cancer using HPPs of 1H-imidazo[4,5-c]quinolin-4-amines or 1H-imidazo[4,5-c]quinolin-4-amine-related Compounds (II)

1 ml of 2% sarcosine 1-isobutyl-1H-imidazo[4,5-c]quinolin-4-amide hydrochloride in 70% ethanol is inhaled to lung twice per day. The process is repeated until the tumor disappears. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 15

Treatment of Skin Cancer using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to the skin on the cancer twice per day. The process is repeated until the tumor disappears If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 16

Treatment of Skin Cancer Before and after Cancer Remove Surgery using HPPs of 1H-imidazo[4,5-c]quinolin-4-amines or 1H-imidazo[4,5-c]quinolin-4-amine-related Compounds Before the surgery, 1 ml of 2% sarcosine 1-isobutyl-1H-imidazo[4,5-c]quinolin-4-amide hydrochloride in 70% ethanol is sprayed to the skin on the tumor twice per day. 3 days before and 3 days after the surgery, the treatment is stopped. 3 days after tumor is removed, 1 ml of 2% sarcosine 1-isobutyl-1H-imidazo[4,5-c]quinolin-4-amide hydrochloride in 70% ethanol is sprayed to the skin around the cancer site or any skin surface of the body twice per day. The process is repeated until the tumor does not show up for 3 months If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 17

Treatment of Genital and Perianal Warts using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to the surface of the warts twice per day. The process is repeated until the tumor disappears. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 18

Treatment of Common Wart, Flat Wart, Filiform Wart, Mosaic Wart, and Any Other Warts using HPPs of 1H-imidazo[4,5-c]quinolin-4-amines or 1H-imidazo[4,5-c]quinolin-4-amine-related Compounds 2% sarcosine 1-isobutyl-1H-imidazo[4,5-c]quinolin-4-amide hydrochloride in 70% ethanol is applied to the surface of the warts twice per day. The process is repeated until the condition is cured. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 19

Treatment of Actinic Keratosis using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to the surface of the actinic keratosis twice per day. The process is repeated until the condition is cured. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body until reddening or swelling disappears.

Example 20

Treatment of Superficial Basal Cell Carcinoma using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to the surface of superficial basal cell carcinoma twice per day. The process is repeated until the condition is cured. If the skin around an application site shows reddening, swelling, or other side effects during the course of treatment is seen, 0.5 ml of 5% N,N-diethylaminoethyl acetylsalicylate hydrochloride in pure water is sprayed to the same skin area or skin on any part of the body until reddening or swelling disappears.

Example 21

Treatment of Superficial Basal Cell Carcinoma using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to the surface of superficial basal cell carcinoma twice per day. The process is repeated until the condition is cured. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 22

Treatment of Bird Flu (Influenza), Swine Flu, and any Other Flu which is caused by influenzavirus a (which includes, but are not limited to H1N1, H2N2, H3N2, H5N1, H7N7, H1N2, H9N2, H7N2, H7N3, H10N7), Influenzavirus B, and/or Influenzavirus C using HPPs of 1H-imidazo[4,5-c]quinolin-4-amines or 1H-imidazo[4,5-c]quinolin-4-amine-related Compounds.

1 ml of 2% sarcosine 1-isobutyl-1H-imidazo[4,5-c]quinolin-4-amide hydrochloride in 70% ethanol is sprayed to upper respiratory system (mouth, throat, nose, et. al) or the skin on neck, chest, or head, or any part of the body twice per day. The process is repeated until the condition is cured. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 23

Prevention of Bird Flu (Influenza), Swine Flu, and any Other Flu which is Caused by Influenzavirus A (which includes, but are not limited to H1N1, H2N2, H3N2, H5N1, H7N7, H1N2, H9N2, H7N2, H7N3, H10N7), Influenzavirus B, and/or Influenzavirus C using HPPs of 1H-imidazo[4,5-c]quinolin-4-amines or 1H-imidazo[4,5-c]quinolin-4-amine-related Compounds Prevention of influenza is very important for high-risk groups, such as children and the elderly, people who have asthma, diabetes, heart disease, or any other chronically ill, people with a weak immune system, such as people with advanced HIV infection or transplant patients (whose immune systems are medically suppressed to prevent transplant organ rejection), suffer from particularly severe disease, and pregnant women. When human influenza pandemics occurs, 1 ml of 2% sarcosine 1-isobutyl-1H-imidazo[4,5-c] quinolin-4-amide hydrochloride in 70% ethanol is sprayed to upper respiratory system (mouth, throat, nose, et. al) or the skin on the neck, head, chest, or any part of the body twice per day. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 24

Treatment of Hepatitis using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is applied to the skin on the back, chest, abdomen, or any other part of the body twice per day. The process is repeated until the condition is cured. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 25

Treatment of Severe Acute Respiratory Syndrome (SARS) using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed to upper respiratory system (mouth, throat, nose, et. al) or the skin on neck, chest, or head, or any part of the body twice per day. The process is repeated until the condition is cured. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 26

Treatment of Pneumonia using HPPs of 1H-imidazo[4,5-c]quinolin-4-amines or 1H-imidazo[4,5-c]quinolin-4-amine-related compounds 1 ml of 2% sarcosine 1-isobutyl-1H-imidazo[4,5-c]quinolin-4-amide hydrochloride in 70% ethanol is sprayed to upper respiratory system (mouth, throat, nose, et. al) or the skin on neck, chest, or head, or any part of the body twice per day. The process is repeated until the condition is cured. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 27

Treatment of Acquired Immune Deficiency Syndrome (AIDS) Using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is applied to the skin on the back, chest, abdomen, or any other part of the body twice per day. The process is repeated until the condition is cured. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 28

Prevention of Acquired Immune Deficiency Syndrome (AIDS) Using HPPs of 1H-imidazo[4,5-c]quinolin-4-amines or 1H-imidazo[4,5-c]quinolin-4-amine-related Compounds 1 ml of 2% sarcosine 1-isobutyl-1H-imidazo[4,5-c]quinolin-4-amide hydrochloride in 70% ethanol is sprayed genital and perianal area or the upper respiratory system (mouth, throat, nose, et. al) twice per day for 2 or more days after exposed to infection or possible infection. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 29

Prevention of Acquired Immune Deficiency Syndrome (AIDS) Using HPPs of 1H-imidazo[4,5-c]quinolin-4-amines or 1H-imidazo[4,5-c]quinolin-4-amine-related Compounds A condom with a therapeutically effective amount of sarcosine 1-isobutyl-1H-imidazo[4,5-c]quinolin-4-amide hydrochloride which is mixed with condom materials or coating (in the form of a solution, spray, lotion, ointment, emulsion or gel) can be used for preventing acquired immune deficiency syndrome (AIDS/HIV) during a possible infection exposure. If the skin around an application site shows reddening, swelling, or other side effects during the course of treatment, 0.5 ml of 5% N,N-diethylaminoethyl acetylsalicylate hydrochloride in pure water is sprayed to the same skin area or skin on any part of the body or inhaled until reddening or swelling disappears.

Example 30

Prevention of Acquired Immune Deficiency Syndrome (AIDS) Using HPPs of 1H-imidazo[4,5-c]quinolin-4-amines or 1H-imidazo[4,5-c]quinolin-4-amine-related Compounds A condom with a therapeutically effective amount of sarcosine 1-isobutyl-1H-imidazo[4,5-c]quinolin-4-amide hydrochloride which is mixed with condom materials or coating (in the form of a solution, spray, lotion, ointment, emulsion or gel) can be used for preventing acquired immune deficiency syndrome (AIDS/HIV) in an unsafe sexual intercourse. If reddening, swelling, or other side effects on or around the application site is seen, 0.5 ml of 5% N,N-diethylaminoethyl acetylsalicylate hydrochloride in pure water is sprayed to the skin on chest, back, abdomen, or any part of the body or inhaled until reddening or swelling disappears.

What is claimed is:

1. A high penetration composition comprising a structure selected form the group consisting of Structure P-1, Structure P-2, Structure P-3, Structure P-4, Structure P-5, Structure P-6, Structure P-7, Structure P-8, Structure P-9, Structure P-10, Structure P-11, Structure P-12, Structure P-14, Structure P-15, Structure P-16, Structure P-17, Structure P-18, Structure P-2A, Structure P-3A, Structure P-4A, Structure P-5A, Structure P-6A, Structure P-7A, Structure P-8A, Structure P-9A, Structure P-10A, Structure P-11A, Structure P-12A, Structure P-14A, Structure P-15A, Structure P-16A, Structure P-17A, and Structure P-18A:

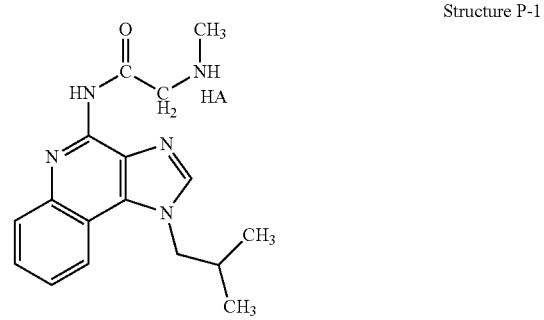

Structure P-1

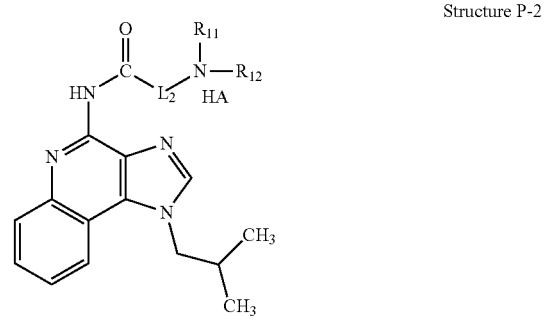

Structure P-2

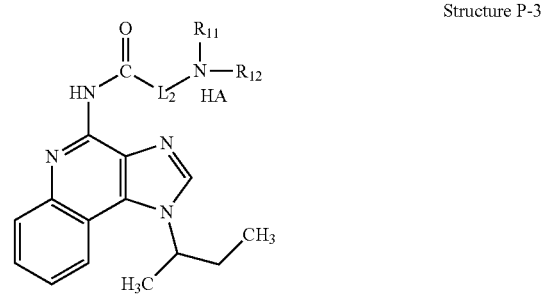

Structure P-3

-continued
Structure P-4
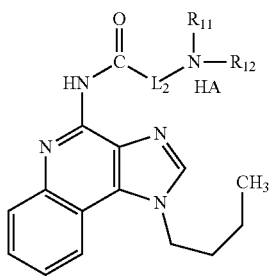
Structure P-5
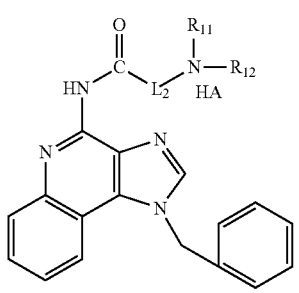
Structure P-6
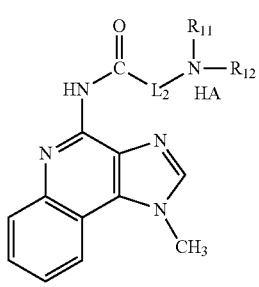
Structure P-7
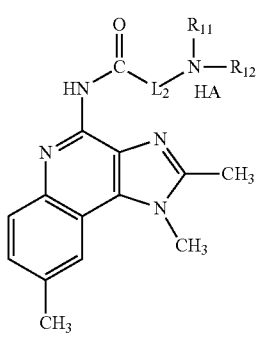
Structure P-8
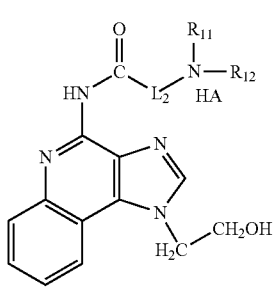
-continued
Structure P-9
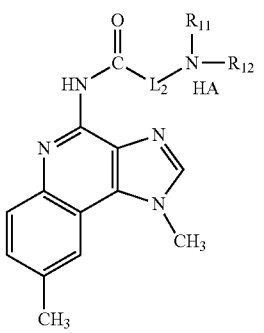
Structure P-10
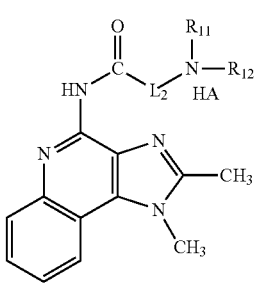
Structure P-11
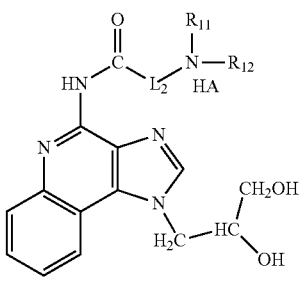
Structure P-12
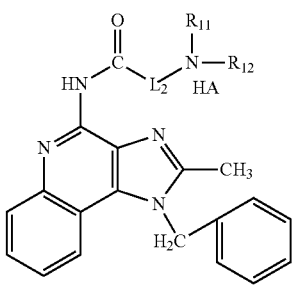
Structure P-14
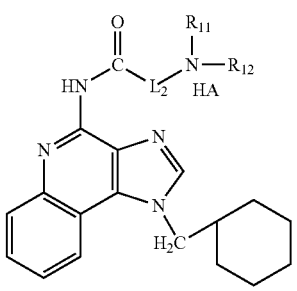

Structure P-15
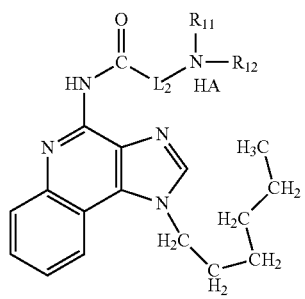
Structure P-16
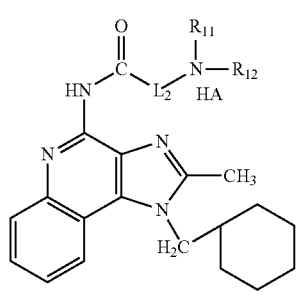
Structure P-17
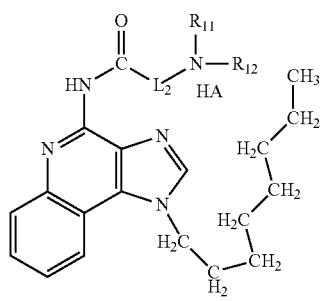
Structure P-18
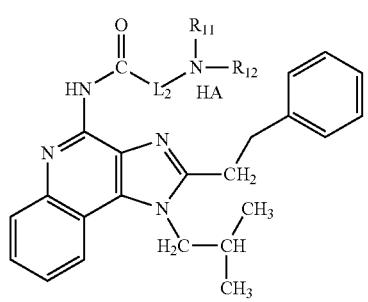
Structure P-2A
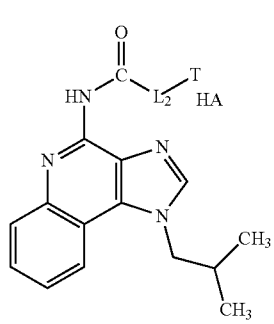
Structure P-14A
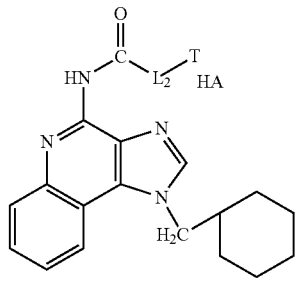
Structure P-3A
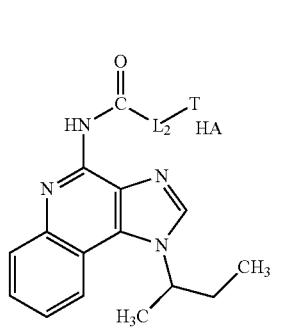
Structure P-4A
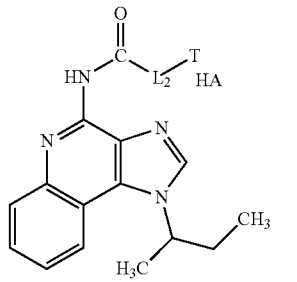
Structure P-5A
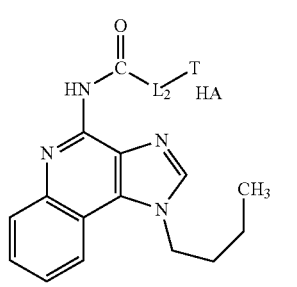
Structure P-6A
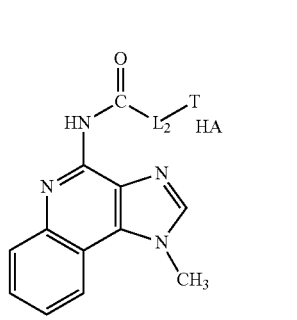

Structure P-7A

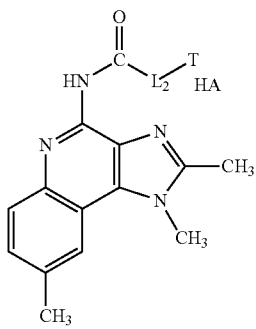

Structure P-8A

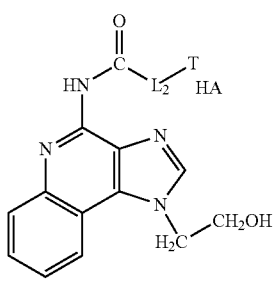

Structure P-9A

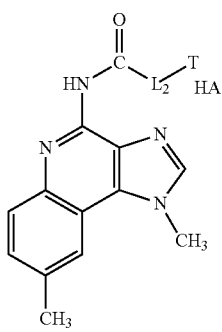

Structure P-10A

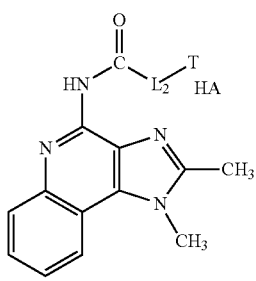

Structure P-11A

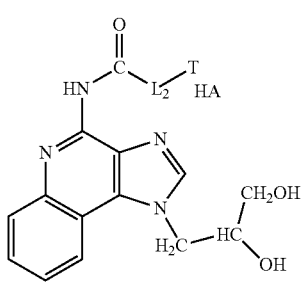

Structure P-12A

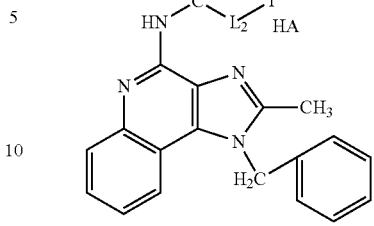

Structure P-15A

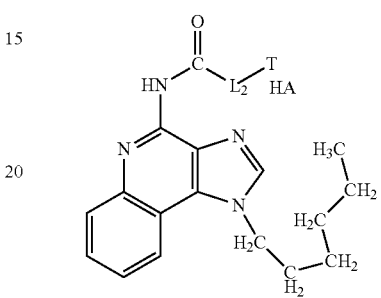

Structure P-16A

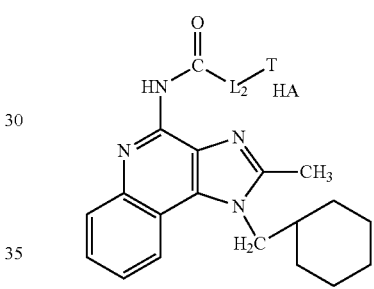

Structure P-17A

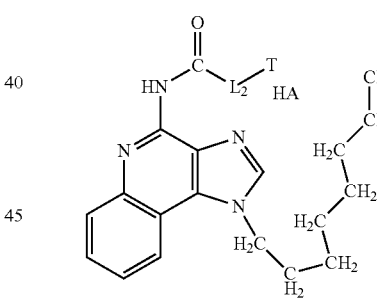

Structure P-18A

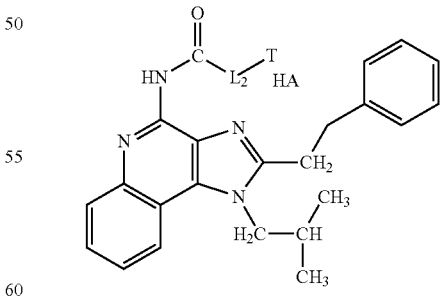

including stereoisomers and pharmaceutically acceptable salts thereof, wherein:

T is selected from the group consisting of Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure No, and Structure Nr:

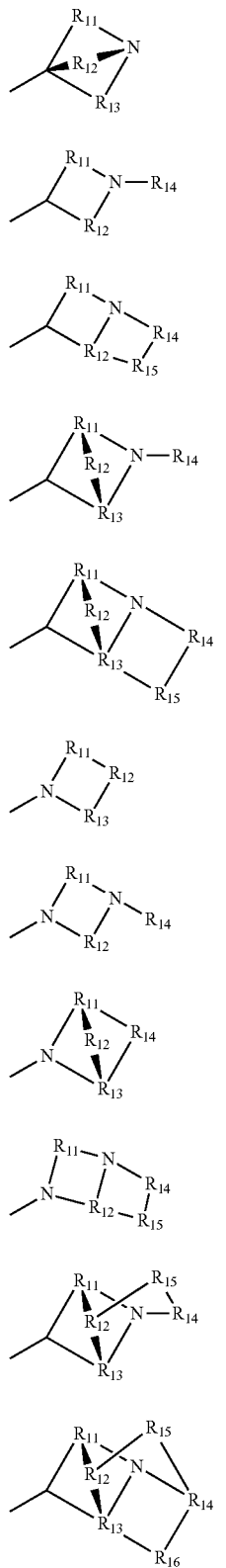

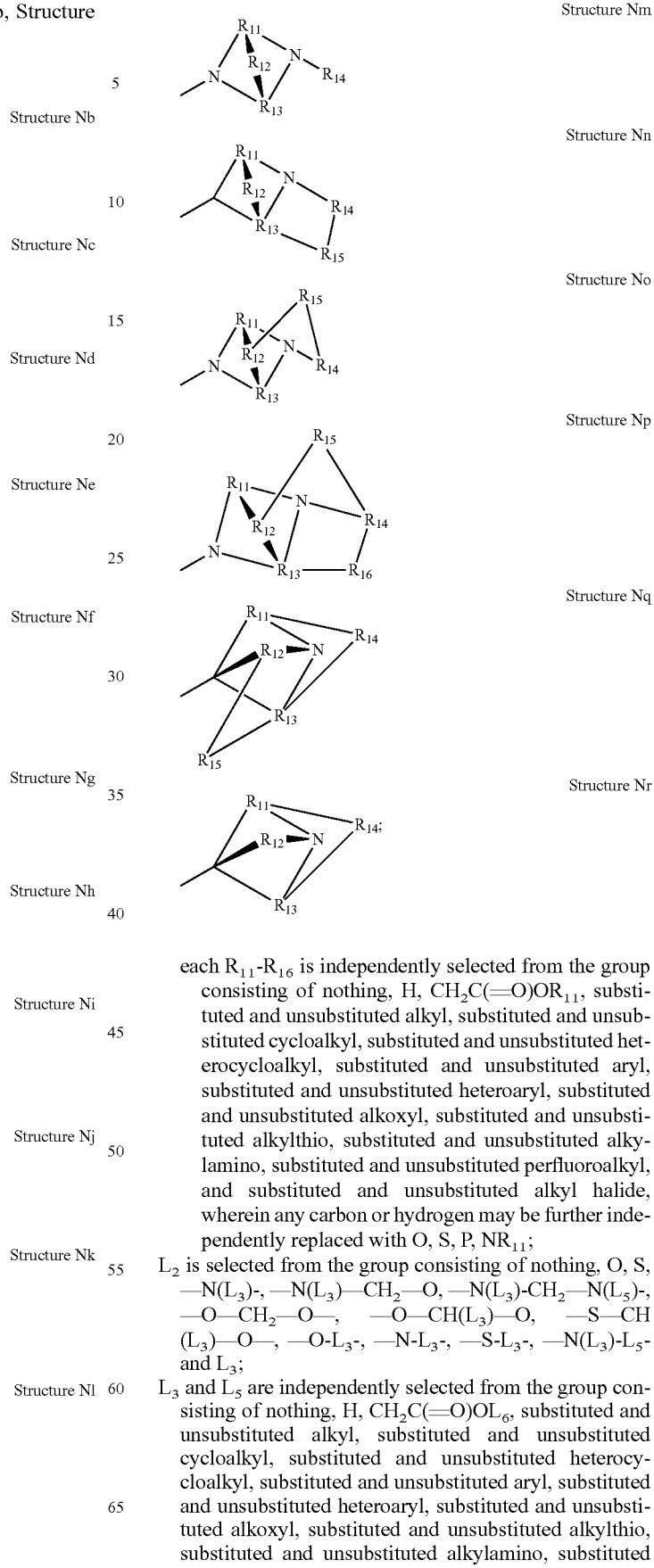

each $R_{11}$-$R_{16}$ is independently selected from the group consisting of nothing, H, $CH_2C(=O)OR_{11}$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_{11}$;

$L_2$ is selected from the group consisting of nothing, O, S, —N($L_3$)-, —N($L_3$)—$CH_2$—O, —N($L_3$)-$CH_2$—N($L_5$)-, —O—$CH_2$—O—, —O—CH($L_3$)—O, —S—CH($L_3$)—O—, —O-$L_3$-, —N-$L_3$-, —S-$L_3$-, —N($L_3$)-$L_5$- and $L_3$;

$L_3$ and $L_5$ are independently selected from the group consisting of nothing, H, $CH_2C(=O)OL_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NL_3$;

$L_6$ is selected from the group consisting of H, OH, Cl, F, Br, I, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_7$, CH=CH, C≡C, $CHL$, $CL_5L_7$, aryl, heteroaryl, or cyclic groups;

$L_7$ is selected from the group consisting of H, OH, Cl, F, Br, I, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_6$, CH=CH, C≡C, $CHL_6$, $CL_6L_5$, aryl, heteroaryl, or cyclic groups; and HA is nothing or a pharmaceutically acceptable acid selected from the group consisting of hydrochloride, hydrobromide, hydroiodide, nitric acid, sulfuric acid, bisulfuric acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

2. A pharmaceutical composition comprising a high penetration composition according to claim 1 and a pharmaceutically acceptable carrier.

3. The pharmaceutical composition according to claim 2, wherein the pharmaceutically acceptable carrier is polar.

4. The pharmaceutical composition according to claim 2, wherein the pharmaceutically acceptable carrier is selected from the group consisting of alcohol, acetone, ester, water, and aqueous solution.

\* \* \* \* \*

UNITED STATES PATENT AND TRADEMARK OFFICE
CERTIFICATE OF CORRECTION

PATENT NO.          : 8,349,866 B2                                    Page 1 of 1
APPLICATION NO.     : 12/534096
DATED               : January 8, 2013
INVENTOR(S)         : Chongxi Yu It is certified that error appears in the above-identified patent and that said Letters Patent is hereby corrected as shown below:

In the Claims

Claim 1, column 57, line 3, replace "No" with --Nq--.

Claim 1, column 59, line 15, replace "CHL" with --$CHL_7$--.

Signed and Sealed this
Seventh Day of May, 2013

Teresa Stanek Rea
*Acting Director of the United States Patent and Trademark Office*